US010385114B2

(12) United States Patent
Mazzolini et al.

(10) Patent No.: US 10,385,114 B2
(45) Date of Patent: Aug. 20, 2019

(54) SPARC (SECRETED PROTEIN, ACIDIC AND RICH IN CYSTEINE), A NEW TARGET FOR THE TREATMENT AND PREVENTION OF ACUTE LIVER FAILURE

(71) Applicants: INIS Biotech LLC, Milford, DE (US); Consejo Nacional de Investigaciones Cientificas Y Tecnicas (Conicet), Ciudad Autonoma de Buenos Aires (AR); Fundacion Instituto Leloir (FIL), Ciudad Autonoma de Buenos Aires (AR); Asociacion Civil de Estudios Superiores (Aces), Ciudad Autonoma de Buenos Aires (AR)

(72) Inventors: Guillermo Daniel Mazzolini, Provincia de Buenos Aires (AR); Estanislao Peixoto, Ciudad Autonoma de Buenos Aires (AR); Jorge Aquino, Provincia de Buenos Aires (AR); Maria C. Atorrasagasti, Ciudad Autonoma de Buenos Aires (AR); Osvaldo Podhjacer, Ciudad Autonoma de Buenos Aires (AR)

(73) Assignees: INIS BIOTECH LLC, Milford, Kent County, DE (US); CONSEJO NACIONAL DE INVESTIGACIONES CIENTIFICAS Y TECNICAS (CONICET), Ciudad Autonoma de Buenos Aires (AR); FUNDACION INSTITUTO LELOIR (FIL), Ciudad Autónoma de Buenos Aires (AR); ASOCIACION CIVIL DE ESTUDIOS SUPERIORES (ACES), Ciudad Autónoma de Buenos Aires (AR)

( * ) Notice: Subject to any disclaimer, the term of this patent is extended or adjusted under 35 U.S.C. 154(b) by 28 days.

(21) Appl. No.: 14/916,948

(22) PCT Filed: Sep. 5, 2014

(86) PCT No.: PCT/IB2014/064295
§ 371 (c)(1),
(2) Date: Mar. 4, 2016

(87) PCT Pub. No.: WO2015/033309
PCT Pub. Date: Mar. 12, 2015

(65) Prior Publication Data
US 2016/0201057 A1    Jul. 14, 2016

Related U.S. Application Data

(60) Provisional application No. 61/874,191, filed on Sep. 5, 2013.

(51) Int. Cl.
| | |
|---|---|
| C12N 15/113 | (2010.01) |
| C07K 14/78 | (2006.01) |
| C07K 16/18 | (2006.01) |
| C12N 15/86 | (2006.01) |

(52) U.S. Cl.
CPC ............ C07K 14/78 (2013.01); C07K 16/18 (2013.01); C12N 15/113 (2013.01); C12N 15/86 (2013.01); C07K 2317/76 (2013.01); C12N 2310/11 (2013.01); C12N 2310/14 (2013.01); C12N 2710/10043 (2013.01); C12N 2740/15043 (2013.01)

(58) Field of Classification Search
CPC combination set(s) only.
See application file for complete search history.

(56) References Cited

U.S. PATENT DOCUMENTS

2007/0031844 A1* 2/2007 Khvorova ............ A61K 31/713
435/6.11

OTHER PUBLICATIONS

Acute Liver Failure (The Mayo Clinic) [online]. [retrieved on Nov. 21, 2017]. Retrieved from the Internet: <https://www.mayoclinic.org/diseases-conditions/acute-liver-failure/symptoms-causes/syc-20352863?p=1>. (Year: 2017).*
Bataller, Ramón, and David A. Brenner. "Liver Fibrosis." Journal of Clinical Investigation 115.2 (2005): 209-218. PMC. (Year: 2005).*
Camino et al., "Adenovirus-mediated inhibition of SPARC attenuates liver fibrosis in rats", Journal of Gene Medicine, vol. 10, No. 9, Sep. 1, 2008, pp. 993-1004.
Catalina Atorrasagasti et al., "Lack of the Matricellular Protein SPARC (Secreted Protein, Acidic and Rich in Cysteine) Attenuates Liver Fibrogenesis in Mice", Plos One, vol. 8, No. 2, Feb. 11, 2013, p. e54962.
Ledda M. F. et al., "Suppression of SPARC expression by anti sense RNA abrogates the tumorigenicity of human melanoma cells", Nature Medicine, vol. 3, No. 2, Feb. 1, 1997, pp. 171-176.
Takayuki Iwaki et al., "Recombinant Adenovirus Vector Bearing Antisense Macrophage Migration Inhibitory Factor cDNA Prevents Acute Lipopolysaccharide-Induced Liver Failure in Mice", Laboratory Investigation, vol. 83, No. 4, Apr. 1, 2003, pp. 561-570.
E. Peixoto et al., "SPARC (secreted protein acidic and rich in cysteine) knockdown protects mice from acute liver injury by reducing vascular endothelial cell damage", Gene Therapy, vol . 22, No. 1, Jan. 1, 2015, pp. 9-19.

(Continued)

*Primary Examiner* — Jennifer Pitrak McDonald
(74) *Attorney, Agent, or Firm* — Muncy, Geissler, Olds & Lowe, P.C.

(57) ABSTRACT

The invention relates to the identification of Secreted Protein, Acidic and Rich in Cysteine (SPARC) as a new therapeutic target in patients with fulminant hepatitis and allows the development of a strategy destined to protect the liver form damage. The invention relates to the treatment of acute liver failure or fulminant hepatitis by administering to a subject in need thereof an agent that inhibits at least partially the expression of SPARC and/or interferes with its biological function.

5 Claims, 36 Drawing Sheets

Specification includes a Sequence Listing.

(56) References Cited

OTHER PUBLICATIONS

Wang, J. C. et al., "Attenuation of fibrosis in vitro and in vivo with SPARC siRNA." Arthritis. Res. Ther. 2010, 12(2): R60, 9 pgs.
Vaquero, J. et al., "Etiology and management of fulminant hepatic failure", Current Gastroenterol. Rep. 2003, 5(1): 39-47.
Piccioni F., et al., "Antitumor effects of hyaluronic acid inhibitor 4-methylumbelliferone in an orthotopic hepatocellular carcinoma model in mice". Glycobiology 2012; 22(3): 400-10.
Lane, T. F. et al., "The Biology of SPARC, A Protein That Modulates Cell-Matrix Interactions", Faseb. J. 1994, 8(2): 163-173.
Francki, A., et al., "SPARC regulates the expression of collagentype I and transforming growth factor-beta1 in mesangial cells", J. Biol. Chem. 1999, 274(45): pp. 32145-32152.
Brekken, R. A. et al., "SPARC, a matricellular protein: at the crossroads of cell-matrix", Matrix Biol. 2000, 19(7): 569-580.
Bradshaw, A. D. et al., "SPARC, a matricellular protein that functions incellular differentiation and tissue response to injury", J. Clin. Invest. 2001, 107(9): 1049-1054.
Bernuau, J., et al., "Fulminant and Subfulminant Liver Failure: definitions and causes", Semin. Liver. Dis. May 1986; 6(2):97-106.
Barker, T. H., et al., "SPARC Regulates Extracellular Matrix Organization Through Its Modulation of Integrin-Linked Kinase Activity", J. Biol. Chem. 2005, 280(43): 36483-36493.
Atorrasagasti C., et al., "SPARC downregulation attenuates the profibrogenic response of hepatic stellate cells induced by TGF-beta1 and PDGF", American journal of physiology. Gastrointestinal and liver physiology 2011; 300(5): G739-48.

\* cited by examiner

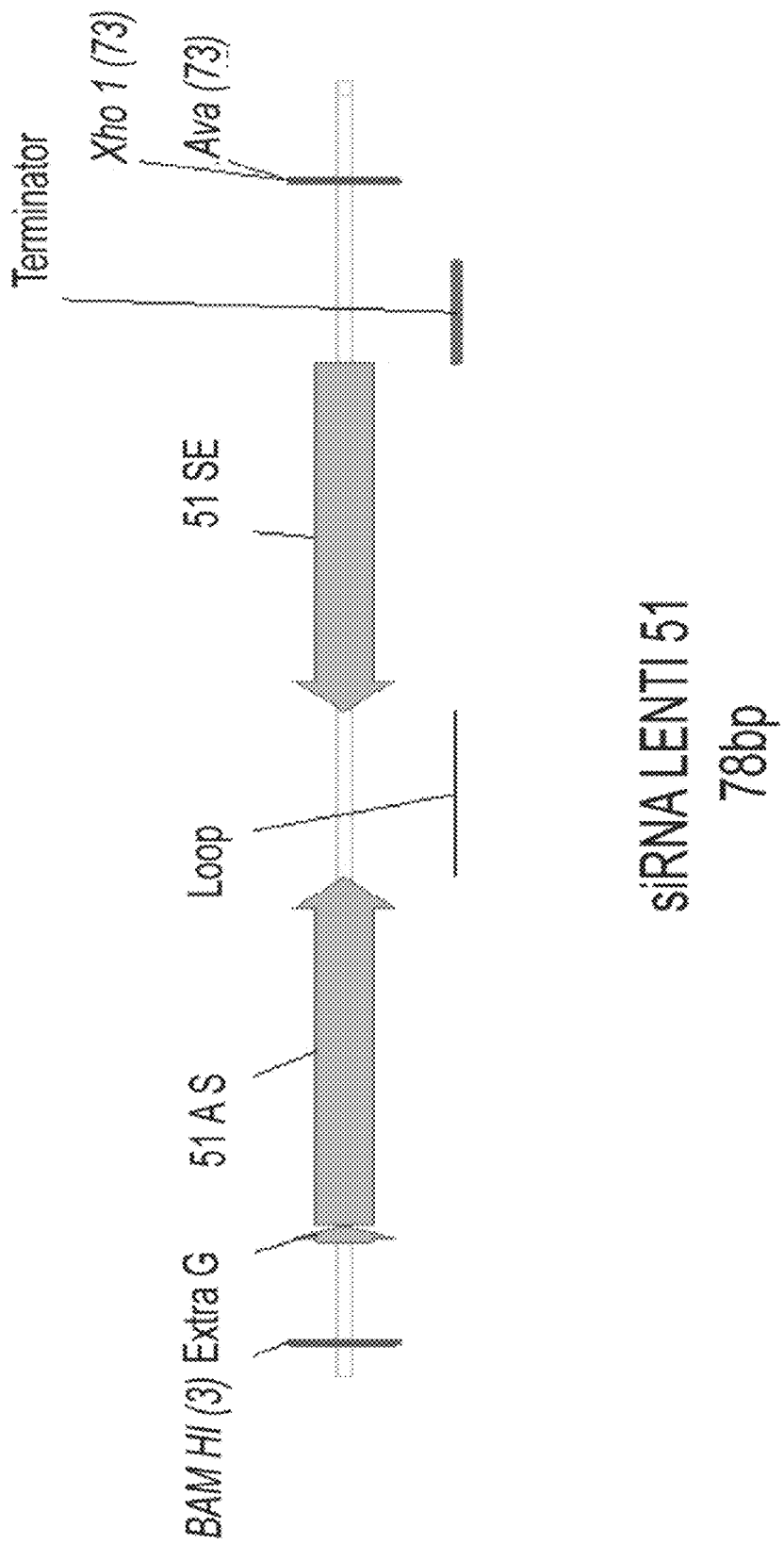

SPARC (SECRETED PROTEIN, ACIDIC AND RICH IN CYSTEINE), A NEW TARGET FOR THE TREATMENT AND PREVENTION OF ACUTE LIVER FAILURE

The present invention relates to the treatment of acute liver failure or fulminant hepatitis. The invention provides the identification of a new therapeutic target in patients with fulminant hepatitis and allows the development of a strategy destined to protect the liver form damage.

PRIOR ART

Secreted protein, acidic and rich in cysteine (SPARC), also called osteonectin or BM-40, is a 43-kDa secreted multifunctional extracellular matrix (ECM) associated glycoprotein involved in many biological processes (Brekken and Sage 2000; Bradshaw and Sage 2001). Among other functions, SPARC plays a major role in the wound healing response to injury and tissue remodeling (Lane and Sage, 1994; Barker et al., 2005). SPARC stimulates collagen deposition, recruitment of inflammatory cells, production of TGF-β1, mesenchymal cell proliferation and synthesis of ECM proteins, induced apoptosis, have anti-adhesive properties (Francki, Bradshaw et al. 1999; Wang, Lai et al. 2010).

In the past, inhibition of SPARC has been proposed as a therapeutic mechanism for treating cirrhosis (Camino et al., 2008; Atorrasagasti et al., 2013), a chronic condition characteristic of liver fibrosis. Following sustained liver injury of different etiologies, hepatic stellate cells become activated and transdifferentiate into myofibroblasts. These myofibroblasts are characterized by excessive collagen synthesis, decreased release of collagen-degrading matrix metalloproteinases (MMPs) and enhanced expression of MMPs inhibitors, which results in an excessive and altered accumulation of hepatic extracellular matrix (ECM). With time, this abnormal accumulation of ECM eventually leads to disorganization of parenchymal architecture and subsequent liver failure.

Fulminant hepatitis, on the other hand, is a clinical syndrome characterized by a sudden liver failure due to autoimmune hepatitis, acute alcohol abuse, viral hepatitis, hepatotoxins, among others (Bernuau and Benhamou, 1999). Although the underlying pathophysiological mechanisms are not fully understood, acute liver failure resulting from fulminant hepatitis is not associated with activation of stellate cells or the abnormal accumulation of hepatic ECM. Thus, the physiological mechanism leading to sudden liver failure seems to be completely different from that of chronic liver disease, suggesting that the therapeutic options available for treating liver fibrosis would not be available for treating acute liver failure. Fulminant hepatitis is a devastating liver disease associated with significant mortality worldwide (40%-80%) (Vaquero and Blei 2003). Liver transplant is the only potential curative option, but due to limited donors the majority of patient dies in the waiting list. Therefore, new therapeutic options are needed for patients with fulminant hepatitis.

SUMMARY OF THE INVENTION

Unexpectedly, the inventors found that SPARC is also a crucial protein in acute liver damage by mediating apoptosis in liver sinusoidal endothelial cells (LSECs), which in turn allows infiltration of activated T-cells into the liver parenchyma, a mechanism of action completely different from that responsible of chronic liver fibrosis.

Accordingly, one object of the present invention is to provide a new therapeutic method for preventing or treating acute liver failure or acute liver damage by administering to a subject in need thereof an agent that inhibits at least partially the expression of SPARC and/or interferes with its biological function. The therapeutic methods of the present invention are thus based on a strategy that is opposed to the one in WO2009150199 and US20110152169A1, which disclose methods comprising administering SPARC for treating liver conditions such as liver inflammation due to autoimmune hepatitis.

According to a first aspect, the present invention comprises a method for the prevention and treatment of acute liver failure or acute liver damage by the use of gene therapy. In one particular embodiment of the method of the invention, a genetic construct that inhibits at least partially the expression of SPARC is administered to a subject in need thereof and used to reduce SPARC expression. In a more particular embodiment, the genetic construct is a vector encoding an antisense RNA molecule which is complementary to SPARC mRNA, such as a recombinant adenovirus, such as the vector AdasSPARC (FIG. 14). In another more particular embodiment of the invention, the genetic construct is capable of expressing a small interfering RNA (siRNA) which inhibits at least partially the expression of SPARC, the genetic construct being for instance a recombinant lentivirus, even more particularly a recombinant lentivirus capable of expressing the siRNA 51 encoded by SEQ ID NO.: 3 or a sequence that is at least 85% identical to SEQ ID NO.: 3, such as the recombinant lentivirus of FIG. 15. In another particular embodiment of the invention, a siRNA or a combination of siRNA molecules that inhibit at least partially the expression of SPARC is administered to a subject in need thereof, such as a siRNA having a sequence selected from SEQ ID NO.: 4, SEQ ID NO.: 5, SEQ ID NO.: 6 and SEQ ID NO.: 7, a sequence that is at least 85% identical to SEQ ID NO.: 4, SEQ ID NO.: 5, SEQ ID NO.: 6 and SEQ ID NO.: 7, and combinations thereof. In yet another particular embodiment of the method of the invention, an agent that interferes with the biological function of SPARC is administered to a subject in need thereof, such as an anti-SPARC antibody, such as a polyclonal or monoclonal antibody. According to another embodiment of the invention, alone or in combination with any of the above embodiments, the inhibition of SPARC expression or the interference with its biological activity occur in the liver.

According to a second aspect, the present invention comprises a pharmaceutical composition for preventing or treating acute liver failure or acute liver damage, said pharmaceutical composition comprising an agent that inhibits at least partially the expression of SPARC and/or interferes with its biological function. According to a particular embodiment, said agent that inhibits at least partially the expression of SPARC is a genetic construct, such as a genetic construct capable of expressing an antisense RNA molecule which is complementary to SPARC mRNA, such as a recombinant adenovirus, such as the vector AdasSPARC (FIG. 14). According to another particular embodiment of the pharmaceutical composition of the invention, the agent that inhibits at least partially the expression of SPARC is a genetic construct capable of expressing a siRNA which inhibits at least partially the expression of SPARC, such as a recombinant lentivirus, such as a lentivirus is capable of expressing the siRNA 51 encoded by SEQ ID NO.: 3 or a sequence that is at least 85% identical to SEQ ID NO.: 3, such as the recombinant lentivirus of FIG. 15. According to another particular embodiment of the invention, it comprises a pharmaceutical composition wherein the agent that inhibits at least partially the expression of SPARC is a siRNA or a combination of siRNA molecules, such as siRNA having a sequence selected from SEQ ID NO.: 4, SEQ ID NO.: 5, SEQ ID NO.: 6 and SEQ ID NO.: 7, a sequence that is at least 85% identical to SEQ ID NO.: 4, SEQ ID NO.: 5, SEQ ID NO.: 6 and SEQ ID NO.: 7, and combinations thereof. In yet another particular embodiment of the method of the invention, the pharmaceutical composition of the invention comprises an agent that interferes with the biological function of SPARC, such as an anti-SPARC antibody, such as a polyclonal or monoclonal antibody.

According to a further aspect, the present invention encompasses the use of an agent that inhibits at least partially the expression of SPARC and/or interferes with its biological function in the manufacture of a pharmaceutical composition for preventing or treating acute liver failure or acute liver damage. According to a particular embodiment, said agent that inhibits at least partially the expression of SPARC is a genetic construct, such as a genetic construct capable of expressing an antisense RNA molecule which is complementary to SPARC mRNA, such as a recombinant adenovirus, such as the vector AdasSPARC (FIG. 14). According to another particular embodiment of the use of the invention, the agent that inhibits at least partially the expression of SPARC is a genetic construct capable of expressing a siRNA which inhibits at least partially the expression of SPARC, such as a recombinant lentivirus, such as a lentivirus is capable of expressing the siRNA 51 encoded by SEQ ID NO.: 3 or a sequence that is at least 85% identical to SEQ ID NO.: 3, such as the recombinant lentivirus of FIG. 15. According to another particular embodiment of the invention, it comprises the use of a siRNA or a combination of siRNA molecules in the manufacture of a pharmaceutical composition for preventing or treating acute liver failure or acute liver damage, such as siRNA having a sequence selected from SEQ ID NO.: 4, SEQ ID NO.: 5, SEQ ID NO.: 6 and SEQ ID NO.: 7, a sequence that is at least 85% identical to SEQ ID NO.: 4, SEQ ID NO.: 5, SEQ ID NO.: 6 and SEQ ID NO.: 7, and combinations thereof. In yet another particular embodiment of the invention, the invention comprises the use of an agent that interferes with the biological function of SPARC, such as an anti-SPARC antibody, such as a polyclonal or monoclonal antibody, in the manufacture of a pharmaceutical composition for preventing or treating acute liver failure or acute liver damage.

According to yet another aspect, the present invention comprises an agent that inhibits at least partially the expression of SPARC and/or interferes with its biological function for use in preventing or treating acute liver failure or acute liver damage. According to a particular embodiment, said agent that inhibits at least partially the expression of SPARC is a genetic construct, such as a genetic construct capable of expressing an antisense RNA molecule which is complementary to SPARC mRNA, such as a recombinant adenovirus, such as the vector AdasSPARC (FIG. 14). According to another particular embodiment of the invention, the agent that inhibits at least partially the expression of SPARC is a genetic construct capable of expressing a siRNA which inhibits at least partially the expression of SPARC, such as a recombinant lentivirus, such as a lentivirus is capable of expressing the siRNA 51 encoded by SEQ ID NO.: 3 or a sequence that is at least 85% identical to SEQ ID NO.: 3, such as the recombinant lentivirus of FIG. 15. According to another particular embodiment of the invention, the agent that inhibits at least partially the expression of SPARC is a siRNA or a combination of siRNA molecules, such as siRNA having a sequence selected from SEQ ID NO.: 4, SEQ ID NO.: 5, SEQ ID NO.: 6 and SEQ ID NO.: 7, a sequence that is at least 85% identical to SEQ ID NO.: 4, SEQ ID NO.: 5, SEQ ID NO.: 6 and SEQ ID NO.: 7, and combinations thereof. In yet another particular embodiment of the invention, it comprises an agent that interferes with the biological function of SPARC, such as an anti-SPARC antibody, such as a polyclonal or monoclonal antibody.

According to yet a further aspect, the present invention relates to a genetic construct capable of expressing an antisense RNA molecule which is complementary to SPARC mRNA, such as a recombinant adenovirus, capable of expressing an antisense RNA molecule which is complementary to SPARC mRNA, such as the vector AdasSPARC (FIG. 14).

According to yet another further aspect, the present invention relates to a genetic construct capable of expressing a siRNA which inhibits at least partially the expression of SPARC, such as a recombinant lentivirus, such as a lentivirus capable of expressing the siRNA 51 encoded by SEQ ID NO.: 3 or a sequence that is at least 85% identical to SEQ ID NO.: 3, such as the recombinant lentivirus of FIG. 15.

According to still another aspect, the present invention relates to a siRNA that inhibits at least partially the expression of SPARC, such as siRNA having a sequence selected from SEQ ID NO.: 4, SEQ ID NO.: 5, SEQ ID NO.: 6 and SEQ ID NO.: 7, a sequence that is at least 85% identical to SEQ ID NO.: 4, SEQ ID NO.: 5, SEQ ID NO.: 6 and SEQ ID NO.: 7.

DESCRIPTION OF THE FIGURES

FIG. 15: Schematic representation of the recombinant lentivirus pRNATin.H1.4-L.51. Virtual design of the plasmid construction pRNATinH1.4 with the sequence 51 (SEQ ID NO.: 3).

DETAILED DESCRIPTION OF THE INVENTION

Figure 1:
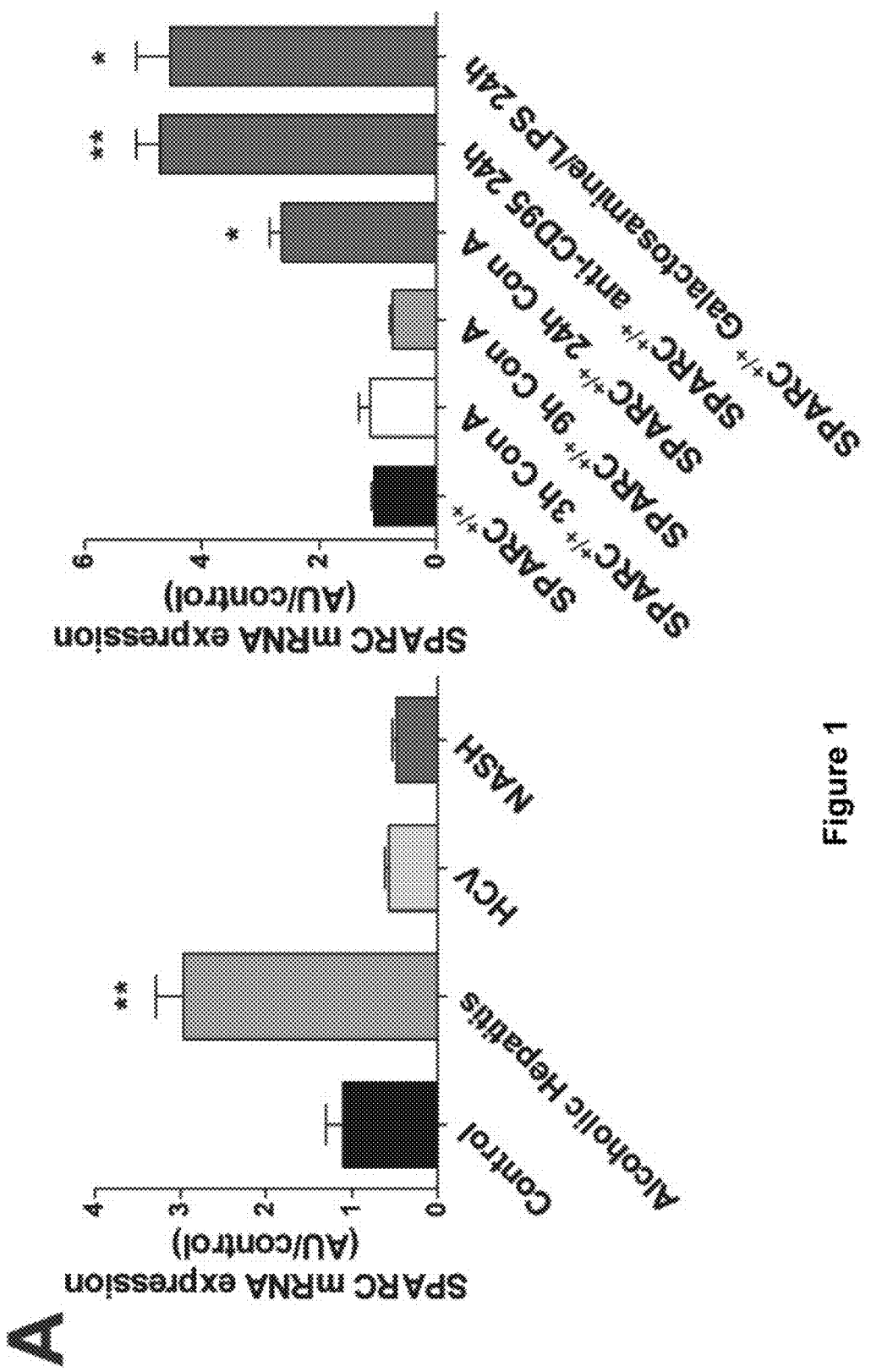
FIGS. 1A-1B: Induction of SPARC expression during acute liver failure. (A) SPARC mRNA expression levels in human and mice liver samples as measured by qPCR. **$p<0.01$ vs control, Fisher's LSD test. *$p<0.05$, **$p<0.01$ vs. SPARC$^{+/+}$, for ConA, GaIN/LPS or anti-CD95 treated mice, Dunn's multiple test. (B) Immunohistochemistry for SPARC. Arrows: endothelial location of SPARC expression (200×).
Figure 1:
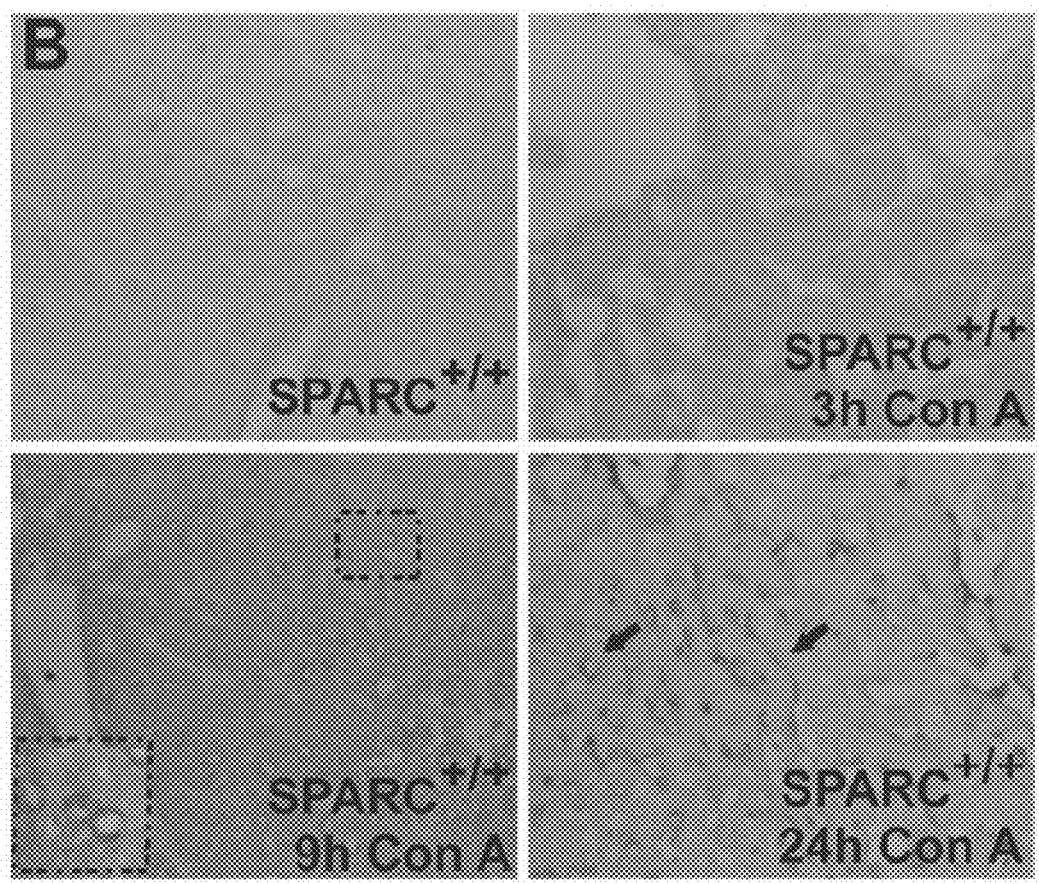

Following the finding that SPARC is overexpressed in samples from patients with alcoholic hepatitis but not in patients with chronic HCV infection or NASH (FIG. 1A), the biological effects of SPARC in acute liver damage were investigated. As a result, the inventors found that SPARC is an essential protein required for the generation of an acute liver damage, revealing it as a target for the prevention and treatment of acute liver failure.

Within the context of the present invention, "to inhibit at least partially the expression" of a protein means to reduce in a physiologically significant degree or even to completely prevent the production of said protein at least in a target tissue, such as in the liver. Such reduction or prevention can be achieved by interfering with any of the steps that normally take place in the expression of proteins, such as interfering with the transcription of the gene encoding for the protein into mRNA and/or interfering with the translation of such mRNA into a polypeptide.

When applied to the expression of a protein, the expression "reduce in a physiologically significant degree" must be understood in the context of the present invention as a reduction in the levels of expression of a protein that are large enough as to have an observable positive impact in the health of the individual in which the expression levels of said protein are reduced, such as avoiding or preventing acute liver failure.

Within the context of the present invention, "to interfere with the biological function" of a protein means to reduce in a physiologically significant degree or even to completely prevent the involvement of said protein in the biological processes in which said protein would normally participate at least in a target tissue, such as in the liver. Such interference takes place after the protein has been expressed, and can be achieved either by targeting the protein itself or its natural partners, such as receptors or other molecules to which said protein normally binds.

In one embodiment of the invention, the agent which inhibits at least partially the expression of SPARC is a genetic construct. A genetic construct is an artificial nucleic acid which acts as a functional unit containing the necessary elements for the transfer or the expression of a particular gene. Many kinds of genetic constructs are well know to those skilled in the art, and include plasmids, viruses, cosmids, and artificial chromosomes. In a particular embodiment of the invention, the genetic constructs used are viral vectors, such as a recombinant adenovirus and a recombinant lentivirus.

In another embodiment of the invention, alone or in combination with any of the embodiments described above or below, inhibition of the expression of SPARC is achieved by means of an antisense RNA molecule which is complementary to SPARC mRNA. The use of antisense RNA to form a duplex with the mRNA of a given protein and thus block its translation is well known in the art, with at least two antisense RNA molecules (fomivirsen and mipomersen) being approved for its use in humans.

According to another embodiment of the invention, inhibition of the expression of SPARC is achieved by means of a small interfering RNA (siRNA). Also known as short interfering RNA or silencing RNA, siRNA are short (usually 20-25 bp) double-stranded RNA molecules which are able to interfere with the expression of genes comprising a nucleotide sequence that is complementary to the siRNA. According to the present invention, the siRNA can be administered to the subject in which inhibition of the expression of SPARC is desired, such as the siRNA of SEQ ID NO.: 4 to SEQ ID NO.: 7 Alternatively, inhibition of the expression of SPARC by siRNA can be achieved by administering, to the subject in which inhibition of the expression of SPARC is desired, a genetic construct capable of expressing said siRNA. Said genetic construct can be for instance a recombinant lentivirus, such as a recombinant lentivirus capable of expressing the siRNA encoded by SEQ ID NO.: 3.

Prevention or treatment of acute liver failure or fulminant hepatitis can also be achieved, according to the present invention, by interfering with the biological function of SPARC. Agents that interfere with the biological function of SPARC include agents that target SPARC directly or agents that target SPARC natural partners, such as agents that competitively inhibit SPARC by binding the same regions on SPARC receptors. Agents which interfere with the biological function of SPARC by targeting SPARC directly include anti-SPARC antibodies, such as polyclonal or monoclonal antibodies.

Techniques for raising antibodies against a desired antigen are well known in the art, typically involving a) administering to a mammal the for which the antibodies are desired under an immunization scheme suitable for eliciting neutralizing antibodies against said chimeric protein; b) obtaining from said mammal a biological sample containing said neutralizing antibodies and/or cells capable of producing said neutralizing antibodies; and c) using said biological sample as a source for said antibody. The biological sample can be of different kinds, and its precise nature will depend upon the particular method by which the antibody is obtained in step c). For instance, the biological sample can be blood, from where serum containing a polyclonal antibody can be obtained. In other embodiments, the biological sample of step b) comprises or consists of B cells, which are used in step c) to produce an antibody-producing hybridoma. The hybridoma technology is well-known to the skilled in the art and has become a standard practice in the field of antibodies. For instance, splenocytes from a mouse immunized against SPARC can be fused with myeloma cells to obtain a monoclonal antibody producing hybridoma. In a more particular embodiment of the invention, the biological sample is blood which contains lymphocytes. From these lymphocytes, genes encoding particular antibodies are obtained and used to recombinantly produce such antibodies which bind specifically to SPARC and thus interfere with its biological function.

Alternatively, antibodies or antigen binding fragments thereof can be recombinantly produced without the need for immunized individuals. These technologies include, but are not limited to, 'repertoire cloning' or 'Fab/phage display', involve the rapid cloning of immunoglobulin gene segments to create immune libraries from which antibodies with desired specificities can be selected. Briefly, a library of variable region genes comprising the desired sequence can be synthetically produced. Each gene of the library is then spliced into a vector, and the vectors are used to display the variable region peptide in the surface of a viral particle or cellular membrane. Antibodies binding to the specific antigen target can be then isolated by a variety of methods, such as paramagnetic beads, fluorescence-activated cell sorting (FACS), and or Enzyme-Linked Immunosorbent Assays (ELISAs). Once a variable region with the desired properties is identified, a full length antibody can be reconstructed by adding the chosen variable region to a constant region, for which expression vectors are available. In recent years, display of whole antibodies has become readily available, to the point that a growing number of companies supply platforms for the display of full-length antibodies. Of course, when complete antibodies rather than just the variable regions are displayed, the step of reconstructing the full length antibody is obviated. Full length antibodies can be then produced in suitable expression systems, most frequently in yeast and mammalian cells. For detailed review of recombinant production of antibodies, see Karu et al. "Recombinant Antibody Technology". ILAR Journal 37 (3):132-141, and Siegel, D. L. 2002. "Recombinant monoclonal antibody technology", Transfus. Clin. Biol. 9 (1):15-22.

According to the present invention, the agents that inhibit at least partially the expression of SPARC and/or interfere with its biological function discussed above are typically contained in a pharmaceutical composition. These active agents are present in the pharmaceutical compositions of this invention at effective physiological doses. The pharmaceutical compositions of the invention comprise the agent that inhibits at least partially the expression of SPARC and/or interferes with its biological function and a pharmaceutically suitable carrier. Pharmaceutically acceptable carriers are well-known to the skilled in the art, and its precise nature depends on the kind of formulation and its intended route of delivery, and include solvents and diluents such as water, saline, dextrose, ethanol, glycerol and the like, dispersants, coatings, stabilizing agents such as albumin and EDTA alkali salts, preserving agents, antibacterial and antifungal agents, isotonic agents, etc. In the case of solid formulations, as those intended for its oral administrations, carriers include manitol, lactose, starch, magnesium stearate, sodium saccharine, talc, cellulose, glucose, sucrose, magnesium carbonate and the like.

The pharmaceutical formulations of the present invention can be in a liquid state or in any other pharmaceutical form known in the art, such as injectable emulsions. The pharmaceutical compositions described in the present invention can also be in tablets, liquid solutions, suspensions or elixirs for oral administration or in sterile liquids such as solutions or suspensions. Preferably an inert medium is used, such as saline media, phosphate-saline buffers and any other medium where the chimeric proteins, nucleotide sequences or segments thereof have a proper solubility.

The pharmaceutical compositions of the invention are useful in a method for preventing or treating acute liver failure or acute liver damage in a mammalian subject, preferably a human subject in need thereof, which is also part of the invention. In said method, said composition is administered to said mammalian subject. The dose, administration schedule and length of treatment will depend on the mammalian species, sanitary condition, age and size of the subject, among other factors, and can be easily determined by those skilled in the art.

To elucidate if SPARC expression could be similarly induced in in vivo models, and to better understand the relationship between SPARC expression and fulminant hepatitis or acute liver failure, 3 models of fulminant hepatitis were generated by the intravenous injection of:

a) concanavalin A (ConA, 15 mg/kg) on SPARC wild-type (SPARC$^{+/+}$) and SPARC$^{-/-}$ mice, b) anti-CD95 antibody Fas-L agonist (Jo2), or c) galactosamine/LPS treatment.

By using the aforementioned models, the inventors demonstrate that SPARC is an essential protein required for the generation of an acute liver damage.

In Vivo Studies

Material and Methods

Patients' Samples

Patients admitted to the Liver Unit, Hospital Clinic of Barcelona with clinical, analytical and histological features of alcoholic hepatitis (AH) from 2007 to 2010 were included in the study. All patients had histological diagnosis of AH (n=34). Liver biopsy was obtained using a transjugular approach. We included a cohort of patients with morbid obesity and associated non-alcoholic steatohepatitis (NASH) (n=10). A laparoscopic liver biopsy was obtained in these patients during bariatric surgery. We also included patients with chronic hepatitis C-induced liver disease (HCV) who did not receive previous antiviral treatment (n=5). As controls, fragments of normal liver tissue were obtained from optimal cadaveric liver donors (n=3) or resection of liver metastases (n=3). The study protocol conformed to the ethical guidelines of the 1975 Declaration of Helsinki and was approved by the Ethics Committee of the Hospital Clinic of Barcelona. All patients gave informed consent.

Animals and Experimental Design

Male C57BL/6×129SvJ (The Jackson Laboratory, Bar Harbor, Me., USA) SPARC$^{+/+}$ and SPARC$^{-/-}$ mice (2-3 months-old) were used. Mice were given a single intravenous injection of ConA (Sigma) at 15 µg/g of body weight as described (Townsend, Scarabelli et al. 2004). Animals were sacrificed at 3, 9 and 24 h after ConA application onset. Other group of animals received a sub-lethal dose (0.25 µg/g) of the agonistic CD95 antibody Jo2 or D-Galactosamine/lipopolysaccharide (GaIN; 0.125 mg/g/LPS; 12.5 µg/kg) and sacrificed at 24 h. Blood and liver samples were obtained in all the cases. Some groups of animals received i.v. administration of 1.3×10$^9$ median tissue culture infective dose (TCID50) of AdasSPARC or Adβgal adenoviruses. For a therapeutic use of siRNA, rat SPARC siRNAs (siSPARC; 4 constructs used in combination: 5'-GAGAAGAACUA-CAACAUGUUU-3' (SEQ ID NO.: 4), 5'-CCAGAACCAU-CAUUGCAA AUU-3' (SEQ ID NO.: 5), 5'-GAACAUUG-CACCACUCGCUUU-3' (SEQ ID NO.: 6), 5'-CUAC-AUCGGACCAUGCAAAUU-3' (SEQ ID NO.: 7)) and a control siRNA (siControl; D-001210-05-05) were purchased from Dharmacon (Chicago, Ill., USA). Mice were given a single i.v. injection of ConA (Sigma) at 10 µg/g body weight. Some groups of animals received via portal vein 1 ml of saline, siControl or siSPARC. Sham-operated animals did not received ConA. Animals were sacrificed at 48 h after ConA application and samples were obtained. Some animals were used for survival analysis. All experimental procedures were performed according to the "Guide for the Care and Use of Laboratory Animals" published by the U.S. National Research Council (National Academy Press, Washington, D.C. 1996) and approved by the School of Medicine, Austral University.

Cell Culture

Human microvascular endothelial cells (HMEC-1) (Centers for Disease Control, Atlanta, Ga., USA) were incubated with DMEM 10% FSB. ConA and chloroquine were incubated at a concentration of 15 µg/ml and 20 µM, respectively.

Biochemical Determination

Serum levels of alanine aminotransaminase (ALT) and asparate aminotransferase (AST) were measured before and 24 h after ConA administration, by standard photometric method using the automated biochemistry analyzer ARCHITECT® (Abbott), according to the manufacturer's instructions. Serum levels of TNF, and IL-6 were measured by Enzyme-Linked Immunosorbent Assay using ELISA kits (R&D Systems) according to manufacturer's instructions.

Quantitative Polymerase Chain Reaction (qPCR)

Liver tissue was homogenized and total RNA was extracted by Trizol Reagent (Sigma-Aldrich Co., USA). RNA (1 µg) was reverse transcribed with 200 U of SuperScript II Reverse Transcriptase (Invitrogen, USA) using 500 ng of Oligo (dT) primers. cDNAs were subjected to qPCR (Table I). SPARC and transforming growth factor-β1 (TGF-β1) mRNA levels were quantified by SYBRR Green (Invitrogen) qPCR (Stratagene Mx3005p, Stratagene, USA) with the following primers: SPARC sense (5'-CCACACG-TTTCTTTGAGACC-3' (SEQ ID NO.: 8)); SPARC antisense (5'-GATGTC CTGCTCCTTGATGC-3' (SEQ ID NO.: 9)); glyceraldehyde-3-phosphate dehydrogenase (GAPDH; used as housekeeping) sense (5'-GGGGCTGCCCA-GAACATCAT-3' (SEQ ID NO.: 10)); GAPDH antisense (5'-GCCTGCTTCACCACCTTCTTG-3' (SEQ ID NO.: 11)); TGF-β1 5'''-ACCAACTATTGCTTCAGCTC-3' (forward) (SEQ ID NO.: 12), 5'''-TGTTGGTTGTAGAGG-GCAAG-3' (reverse) (SEQ ID NO.: 13). All PCR amplifications were carried out using 40 cycles of 95° C. for 30 s, 55° C. for 30 s, and 72° C. for 30 s. For liver human biopsies, qPCR reactions were carried out in a StepOnePlus™ Real-Time PCR System using commercial primer-probe pairs (Applied Biosystems, Foster City, Calif., USA). mRNA levels for human SPARC were measured. 18S RNA was used as the endogenous control. Gene expression values were calculated based on the ΔΔCt method. The results were expressed as 2-ΔΔCt referred as fold increase compared with the mean expression quantified on normal livers.

Histological Analysis and Immunostaining

Liver samples were fixed in 10% formalin and then paraffin-embedded. Tissue was dehydrated, embedded in paraffin, and stained by H&E. Chromogenic immunohistochemistry for SPARC and CD4 was performed as described elsewhere 4. In fluorescent immunocytochemistry, cultured HMEC-1 cells, siSPARC lentivirus transfected or siSCR (scrambled siRNA lentivirus-infected cells) were stained with anti-LC3 antibody (1:50, Abgent, USA), using an anti-rabbit Alexa 488-conjugated IgG secondary antibody (1:200, Promega, USA). For in situ detection of apoptotic cells, terminal deoxynucleotidyl transferase-mediated labeling of nick-end DNA (TUNEL) staining was performed on cryosections, according to manufacturer's instructions (Calbiochem, Germany). In fluorescent immunohistochemistry, frozen liver sections were stained using an anti-VCAM (1:25, BD, USA) primary antibody and an anti-rat Cy3-conjugated IgG secondary antibody (1:400, Jackson, USA).

Apoptotic cells were quantified by acridine orange and ethidium bromide staining as described elsewhere (Piccioni et al., 2012). Phalloidin staining was performed as previously described (Atorrasagasti et al., 2011). Pictures were taken using a Nikon DN100 CCD camera mounted onto a Nikon Eclipse E800 microscope.

Flow Cytometric Analysis

CD4 and CD8+ cells were determined by flow cytometry of liver tissue homogenate. Briefly, the mice were sacrificed 24 h after ConA administration, liver tissue were excised, and single cell suspensions were prepared by mechanical disruption in Hanks balance salt solution (Buffer Hanks plus 10% fetal bovine serum) with 0.5 mg/ml collagenase (Sigma) using the back of a 10 ml syringe. After incubation at 37° C. for 45 min cell suspension was washed and filtered through a 70 µm mesh (BD biosciences. Cell suspension was treated with red blood cell lysis buffer (0.15 M NH4Cl, 1 mM $KHCO_3$, 0.1 mM Na2-EDTA), and washed with PBS 1% BSA. Cell suspension staining were carried with anti-mouse PE conjugated antibodies against CD8 and anti-mouse FITC conjugated antibodies against CD4 (BDBiosciences) following standard procedures. Samples were analyzed using a FACSscalibur flow cytometer (Becton Dickinson), and data acquired were analyzed using WnMDI 2.8 software (Scripps Institute, La Jolla, Calif.).

Electron Microscopy

After 6 h, ConA treated animals were sacrificed and hepatic tissue obtained. Liver sections of 1 $mm^3$ were fixed in 2.5% glutaraldehyde in PBS for 10 min, rinsed three times for 5 min in PBS and further fixed with 1% osmium tetraoxide at RT for 1 h. After rinsing in distilled water, sections were dehydrated with graded series of ethanol. Sections were then embedded in a gelatin capsule containing epoxy resin and incubated at 60° C. for 48 h for polymerization. Ultrathin sections (50 nm) were made and observed under a Hitachi H-7000 electron microscope (Hitachi, Tokyo, Japan).

Generation of Recombinant Adenoviral Vectors.

Figure 14:
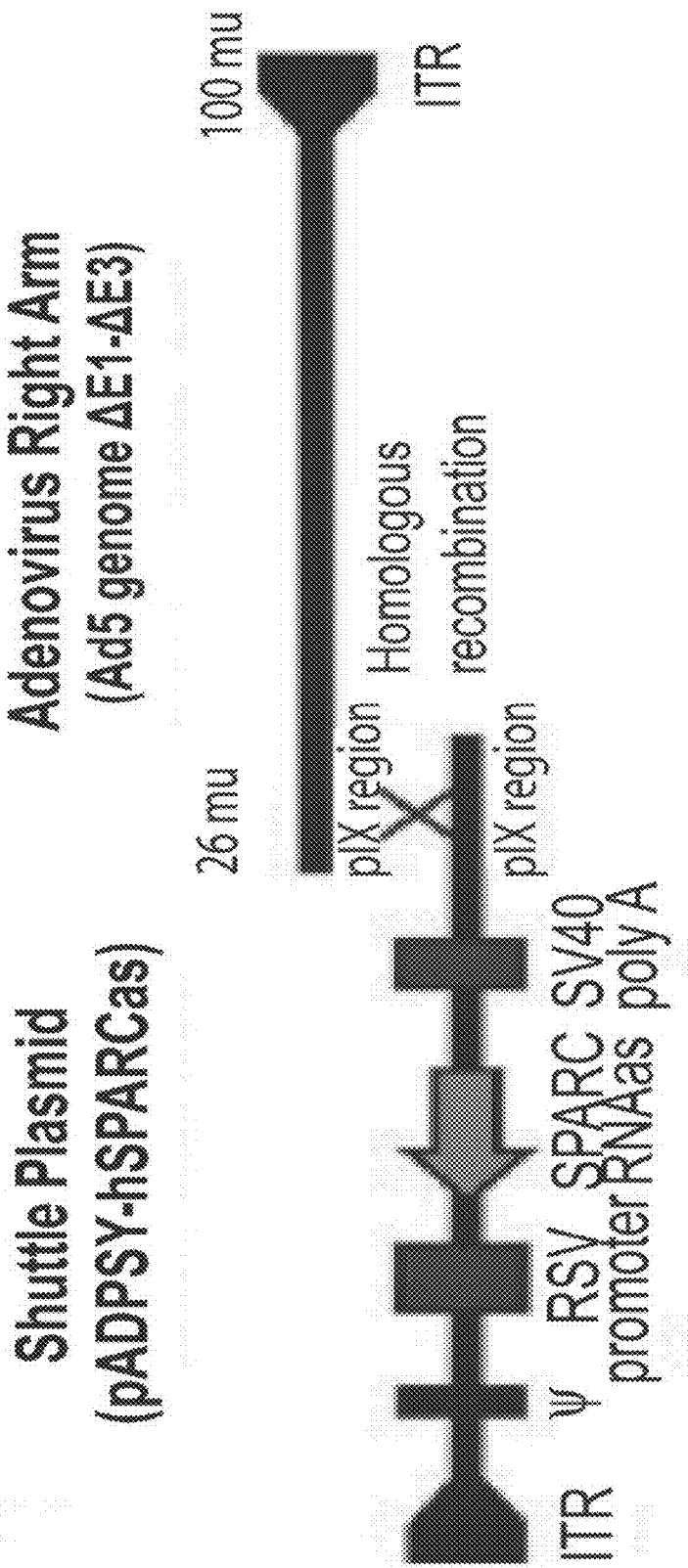
FIG. 14: Schematic representation of the recombinant adenovirus AdasSPARC. This vector carries the coding sequence of human SPARC cDNA in antisense under the control of RSV promoter. The fragment was cleaved with restriction enzyme Sa/I.

AdasSPARC (FIG. 14), an adenovirus encoding for SPARC antisense full-length sequence and Adβgal were constructed and produced as described elsewhere (Camino et al., 2008). Lentivirus vectors were produced as follows. pRNATin.H1.4-L.51 vector containing siSPARC sequence TGGATCCCGCGGCAGGCAGAGCGCGCTCTCTT GA-TATCCGGAGAGCGCGCTCTGCCTGCCGTTTTTTC-CAACTCGAGG (SEQ ID NO.: 3) was produced following the Genscript cloning protocol. Scramble control vector was ordered from Genscript. Lentiviral vectors were produced using The ViraPower™ Lentiviral Technology (Invitrogen). Briefly, 293 FT cells were transfected with a mixture of 36 µl Lipofectamine 2000 (Invitrogen), 9 µg (9 µl) of ViraPower™ Packaging Mix and 3 µg of the pRNAT-in.H1.4-L.51 (siSPARC, FIG. 15) or scramble (siSCR) expression plasmid DNA in 1 ml of Opti-MEMR I Medium without serum. Lentivirus-containing supernatants were collected after 48-72 h post transfection. Supernatant was used for 48 h to transduce HMEC-1 cells.

Transmigration and Cell Adhesion Assay

Cell adhesion was performed as previously described (Atorrasagasti et al., 2011) To analyze splenocytes transmigration through non-transfected, siSPARC or siSCR lentivirus transfected HMEC-1 cell monolayers, pretreated for 3 h with ConA, a total number of $1 \times 10^5$ HMEC-1 cells were seeded on the top of 8 µm pore polycarbonate filters of 24-transwell units (Falcon, BD Labware) coated with 10 µg/ml fibronectin. HMEC-1 cells were allowed to attach overnight at 37° C. CCL19 and CCL21 (10 ng/µl) were then placed in the lower chamber as splenocyte chemoattractants. DAPI pre-stained splenocytes ($5 \times 10^5$) were placed on the top of confluent HMEC-1 cells and were allowed to transmigrate for 4 h at 37° C. After that, the membrane was carefully removed and cells on the upper side of the membrane were scraped off. Cells attached to the lower side of the membrane were fixed in 2% formaldehyde. Cells were counted using fluorescent-field microscopy and images captured in three representative visual fields (10×) were analyzed using CellProfiler software (www.cellprofiler.com), and the mean number of cells/field was obtained.

Microarray Analysis

Samples were processed following Microarrays Inc. (Nashville, USA) recommendations and aRNA was hybridized to 48.5K Exonic Evidence-Based Oligonucleotide (HEEBO) arrays. The microarray signal intensity was evaluated using SpotReader software (Niles Scientific, USA). Normalisation was performed in an R statistical environment using the Limma package (http://www.r-proyect.org). Raw data from the individual arrays were processed using standard and normexp background correction 30 and print-tip loess normalisation 31. For normalisation in between arrays, the global scale normalisation function with median absolute deviation was used 32. Heatmaps were constructed using MeV software 33. The gene ontology (GO) analysis was performed using DAVID Bioinformatics Resources 6.7 (http://david.abcc.ncifcrf.gov/) 34, and a pathway analysis was performed with the use of Ingenuity Pathway Analysis (IPA, Ingenuity Systems, www.ingenuity.com).

Statistical Analysis

Data are expressed as mean±SEM when appropriate. Statistical analysis was performed using Student's t test or Mann-Whitney when distribution is not normal. Differences were considered to be significant when $p<0.05$.

Results

Figure 2:
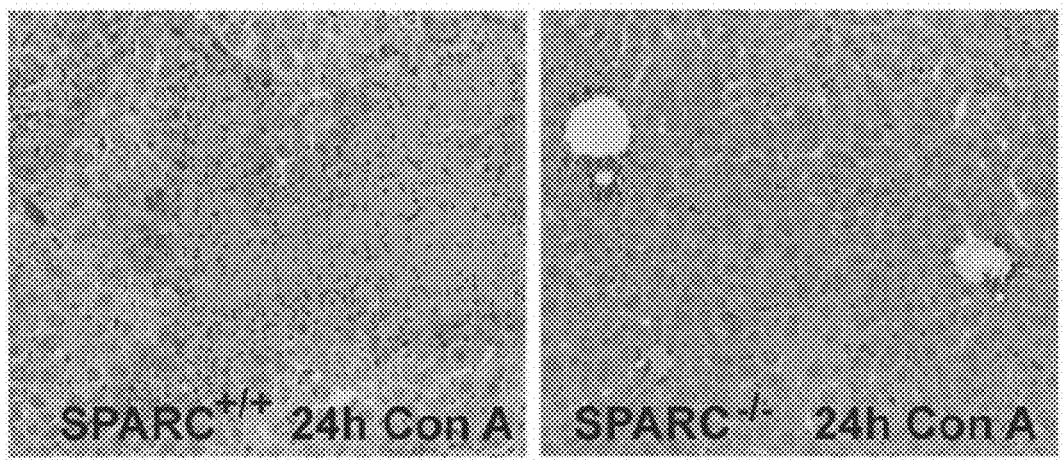
FIG. 2. Reduced ConA-Induced Hepatitis in SPARC knockout mice. Representative photomicrographs of liver sections stained with H&E from 24 h ConA-treated SPARC$^{+/+}$ or SPARC$^{-/-}$ mice. Original magnification 200×.
Figure 3:
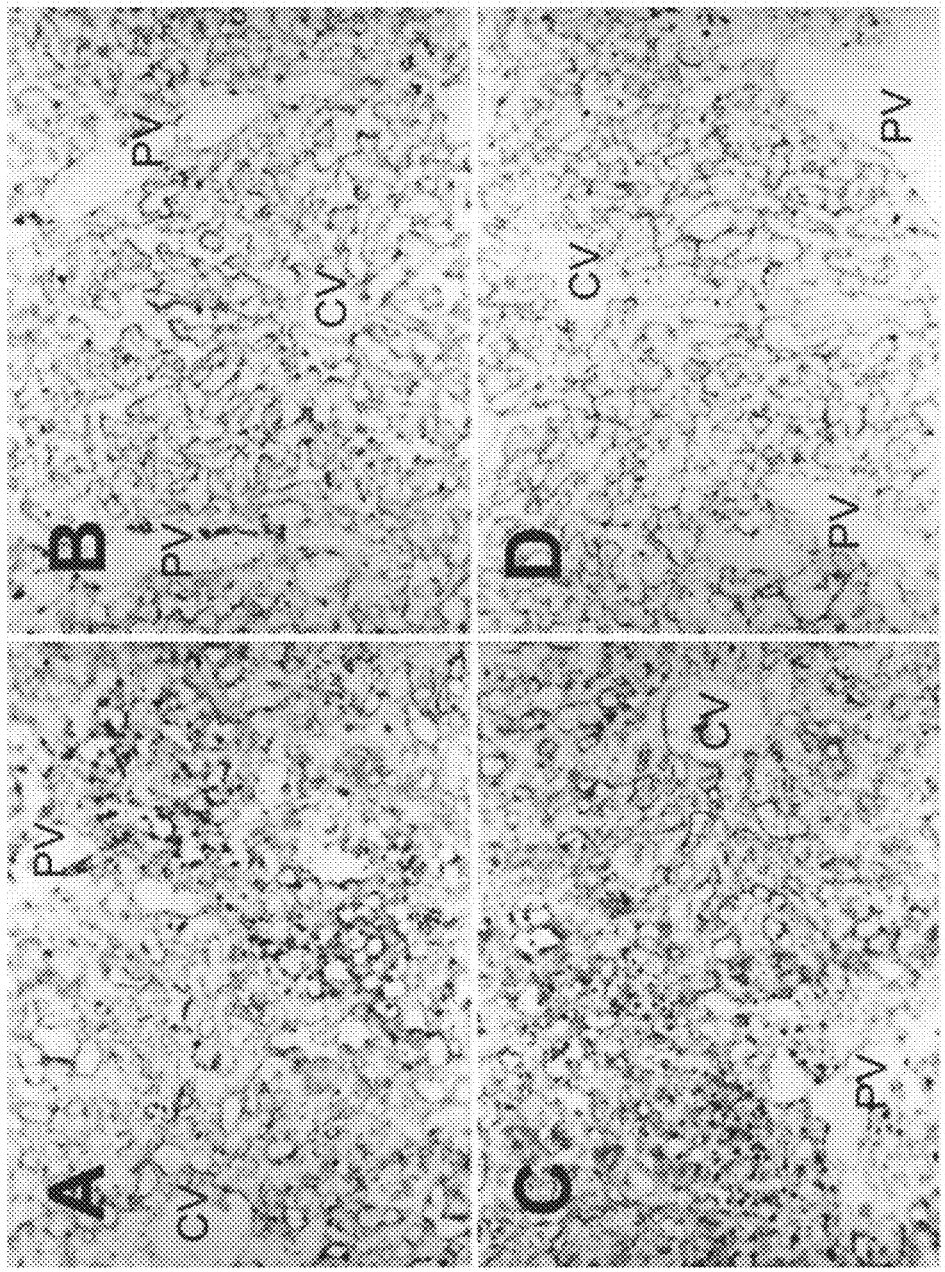
FIGS. 3A-3I. Reduced CD4+ and CD8+ cells infiltration in SPARC knockout liver. Representative photomicrographs of liver sections immunostained with CD4 (A, B) or CD8 (C, D) from SPARC$^{+/+}$ mice (A, C) or SPARC$^{-/-}$ mice (B, D) 24 h ConA-treated. Pv, portal vein; CV, central vein. E) Morphometric quantification of positive CD4+ cells *$p<0.05$, Mann-Whitney test. F) Morphometric quantification of positive CD8+ cells *$p<0.05$, Mann-Whitney test. G) Quantification of inflammatory cells in liver parenchyma after 24 h ConA administration H) Flow citometry of liver tissue homogenate for CD4+ cells quantification SPARC$^{+/+}$ mice or SPARC$^{-/-}$ mice 24 h ConA-treated *$p<0.05$, ***$p<0.001$, Mann-Whitney test. I) Flow cytometry of liver tissue homogenate for CD8+ cells quantification SPARC$^{+/+}$ mice or SPARC$^{-/-}$ mice 24 h ConA-treated *$p<0.05$, ***$p<0.001$, Mann-Whitney test.
Figure 3:
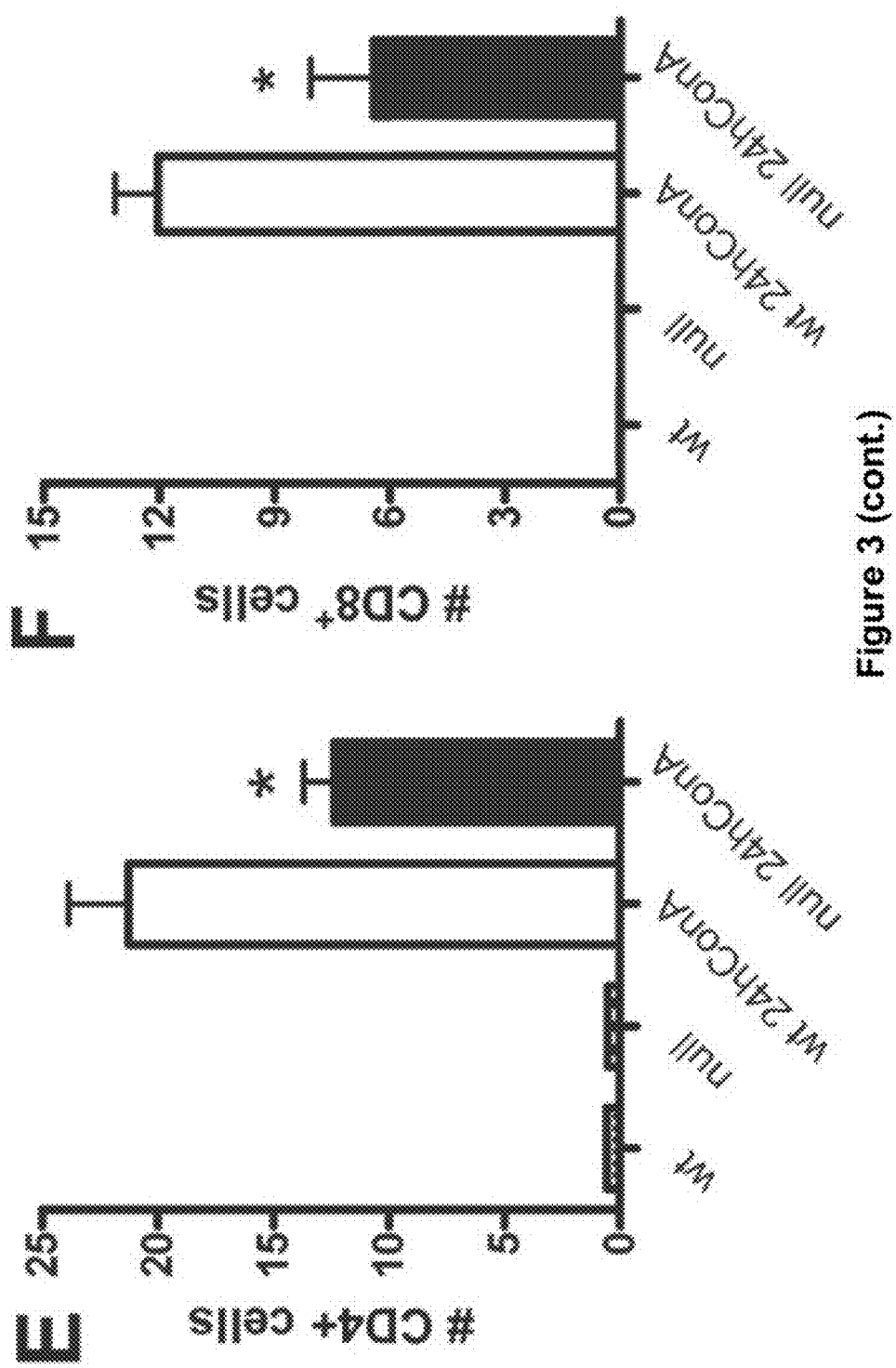
Figure 3:
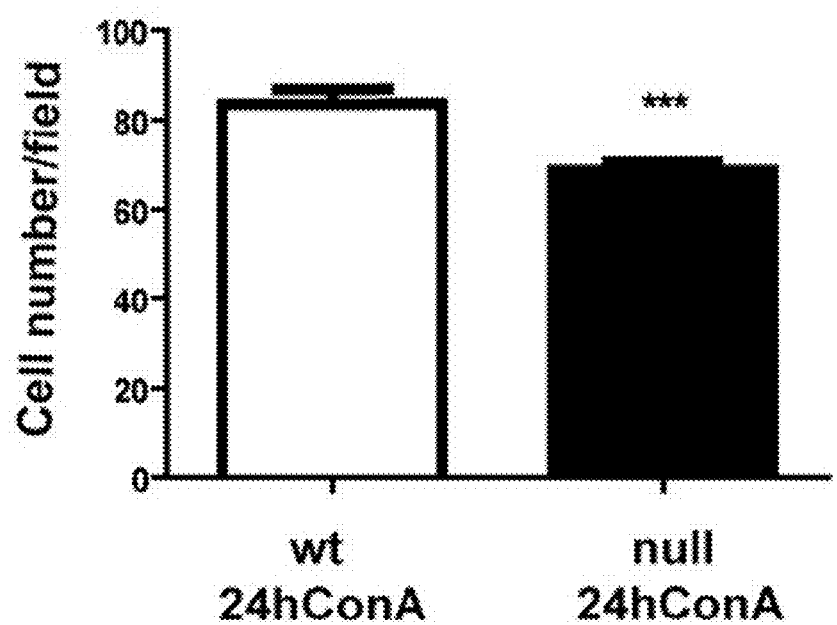
Figure 3:
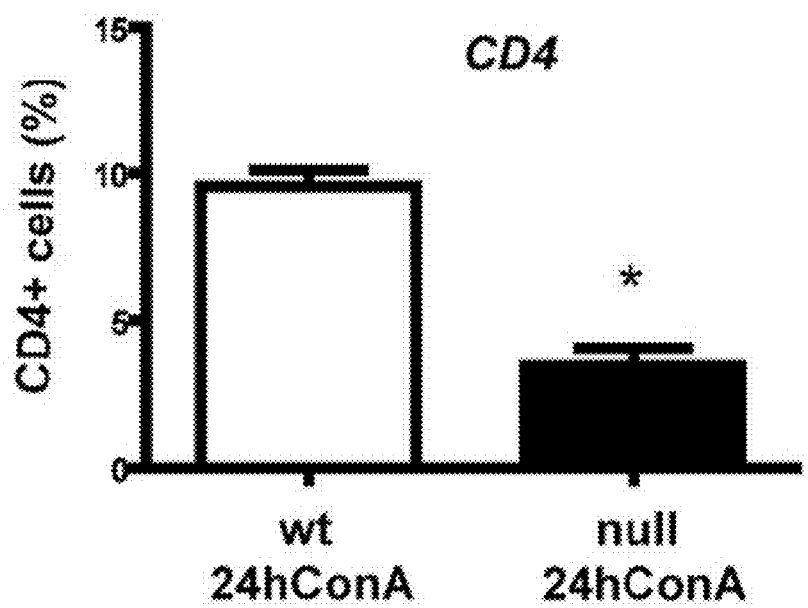
Figure 3:
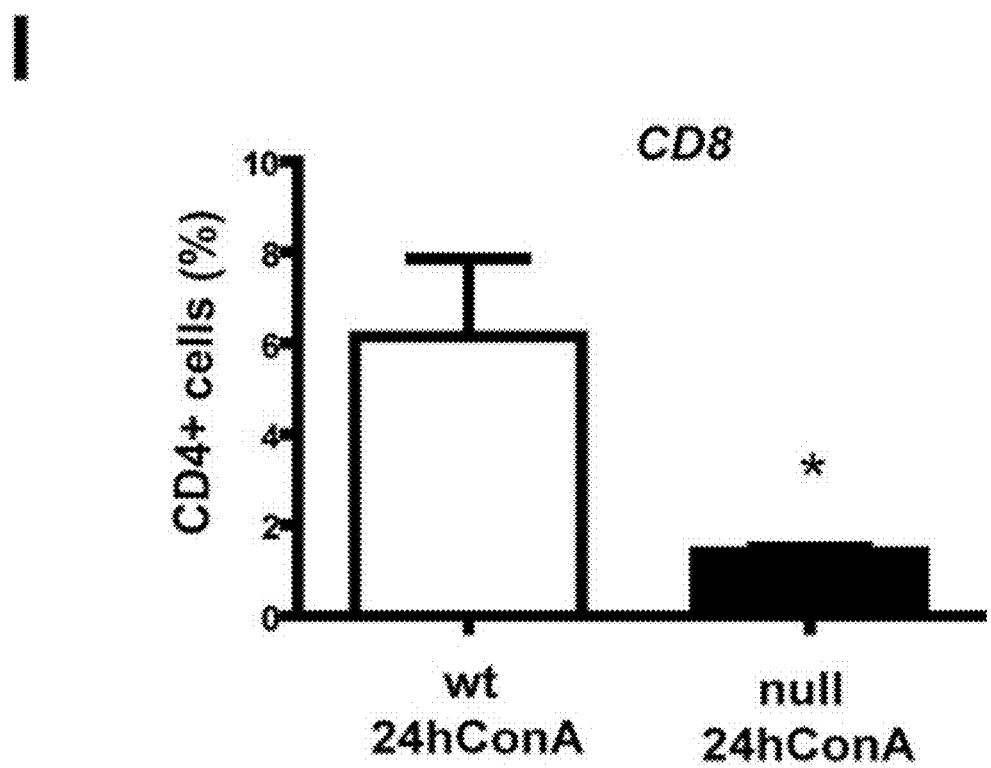
Figure 4:
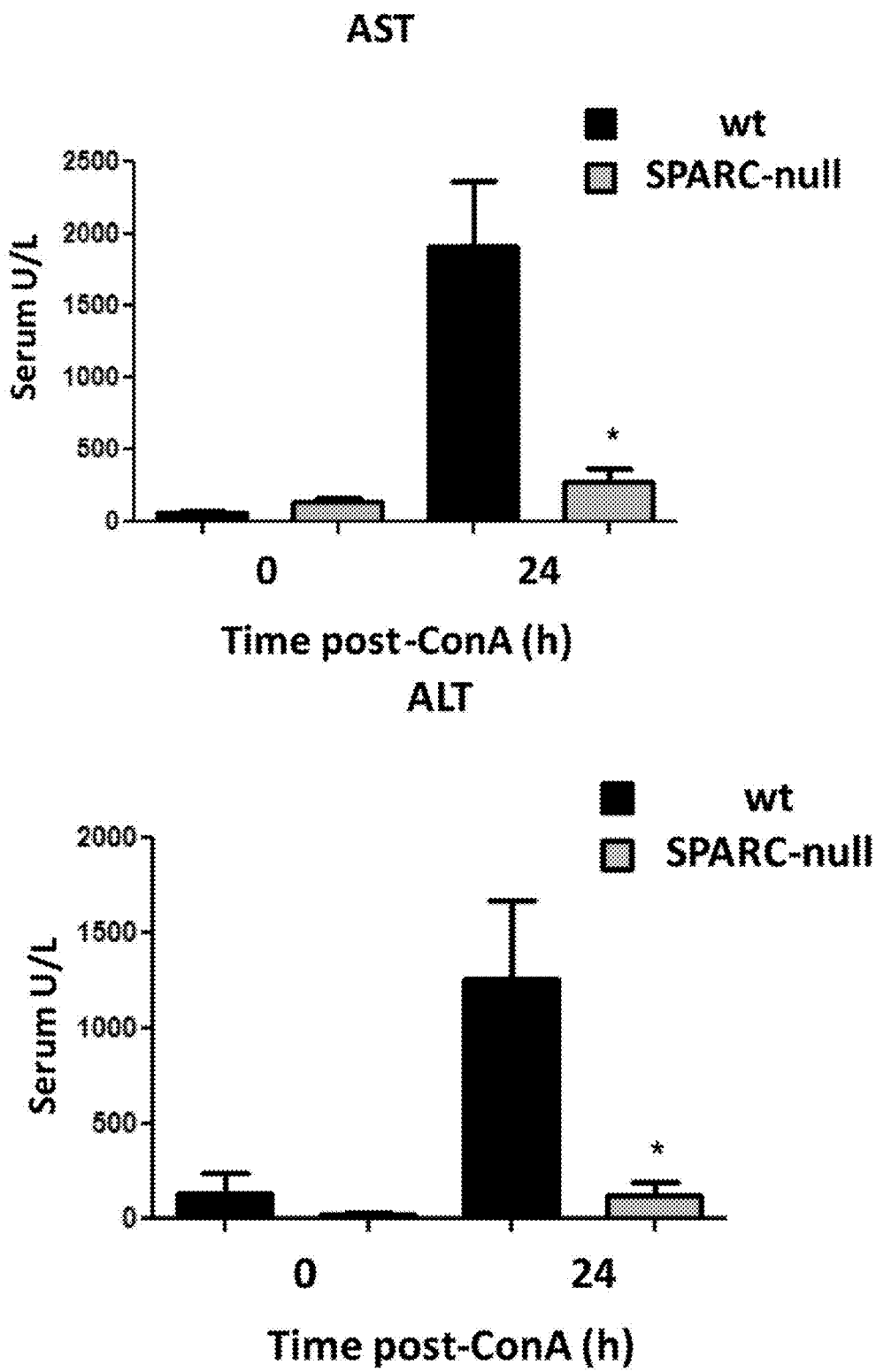
FIG. 4. Reduced transaminase levels ConA-Induced Hepatitis in SPARC knockout mice. Aspartate aminotransferase (AST) and alanine aminotransferase (ALT) serum levels in SPARC$^{+/+}$, SPARC$^{-/-}$ or in 24 h ConA-treated SPARC$^{+/+}$ or SPARC$^{-/-}$ mice.
Figure 5:
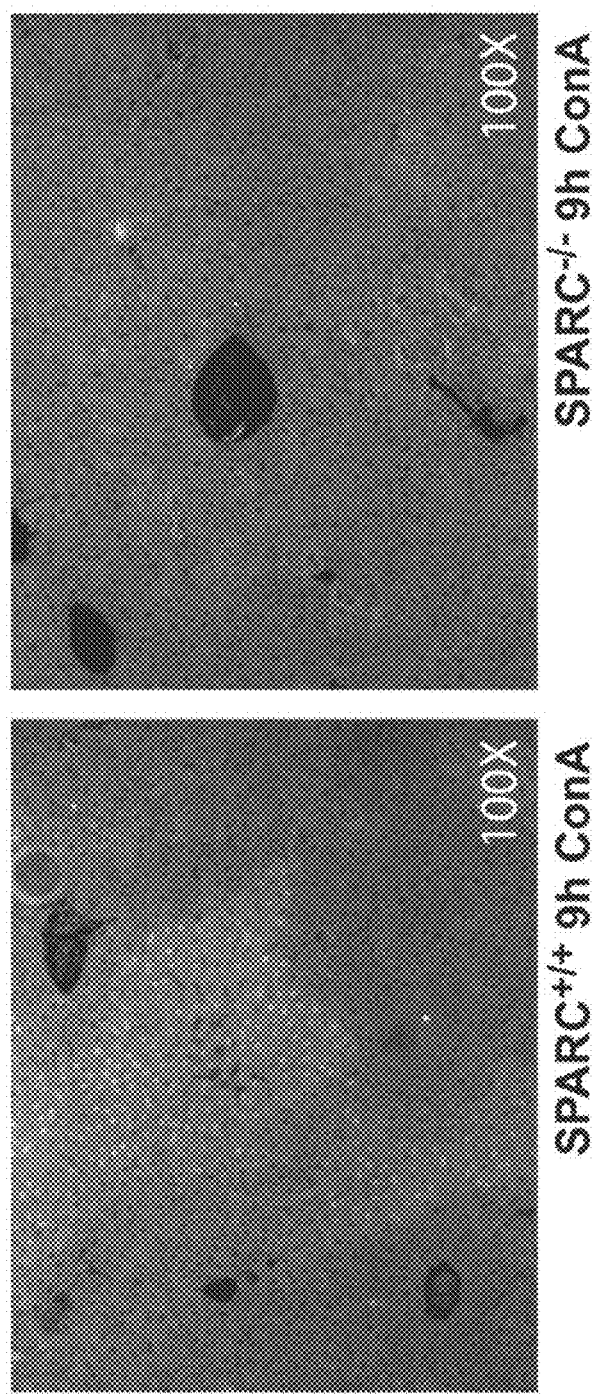
FIG. 5. Reduced apoptotic cells in ConA-Induced Hepatitis in SPARC knockout. Apoptosis TUNEL assay in liver tissue from 9 h ConA-treated SPARC$^{+/+}$ or SPARC$^{-/-}$ mice.
Figure 6:
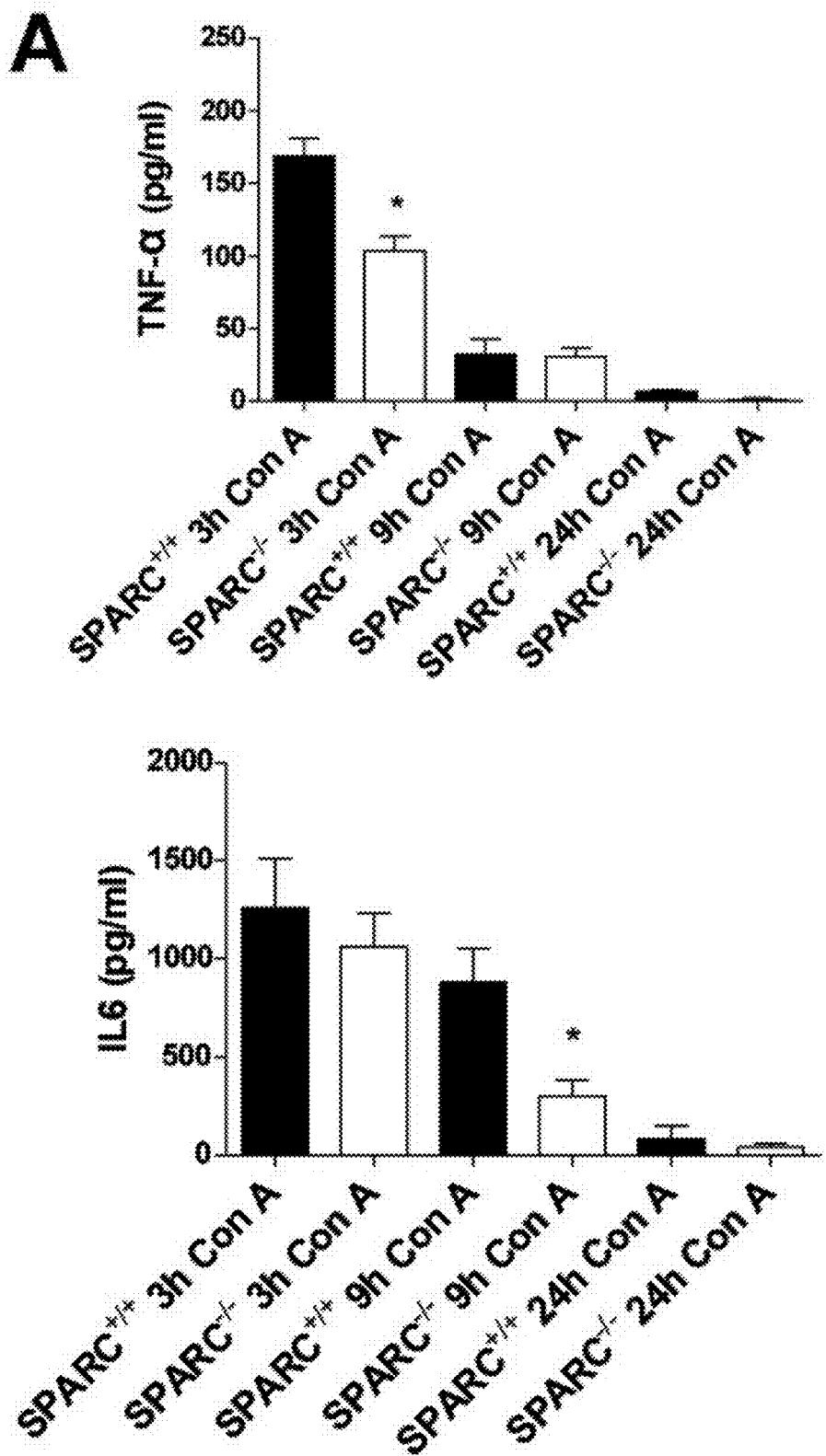
FIGS. 6A-6B. Reduced serum levels of TNFα and IL-6 and downregulation of TGF-β1 hepatic expression in ConA-treated SPARC deficient mice. (A) Serum levels of TNFα and IL-6. *p<0.05 SPARC$^{-/-}$ 3 h ConA vs. SPARC$^{+/+}$ 3 h ConA for TNFα and SPARC$^{-/-}$ 9 h ConA vs. SPARC$^{+/+}$ 9 h ConA for IL-6, Mann Whitney test. (B) qPCR for TGF-β mRNA; ****p<0.0001 SPARC$^{-/-}$ 9 h ConA vs. SPARC$^{+/+}$ 9 h ConA and *p<0.05 SPARC$^{-/-}$ 24 h ConA vs. SPARC$^{+/+}$ 24 h ConA, Dunn's multiple test.
Figure 6:
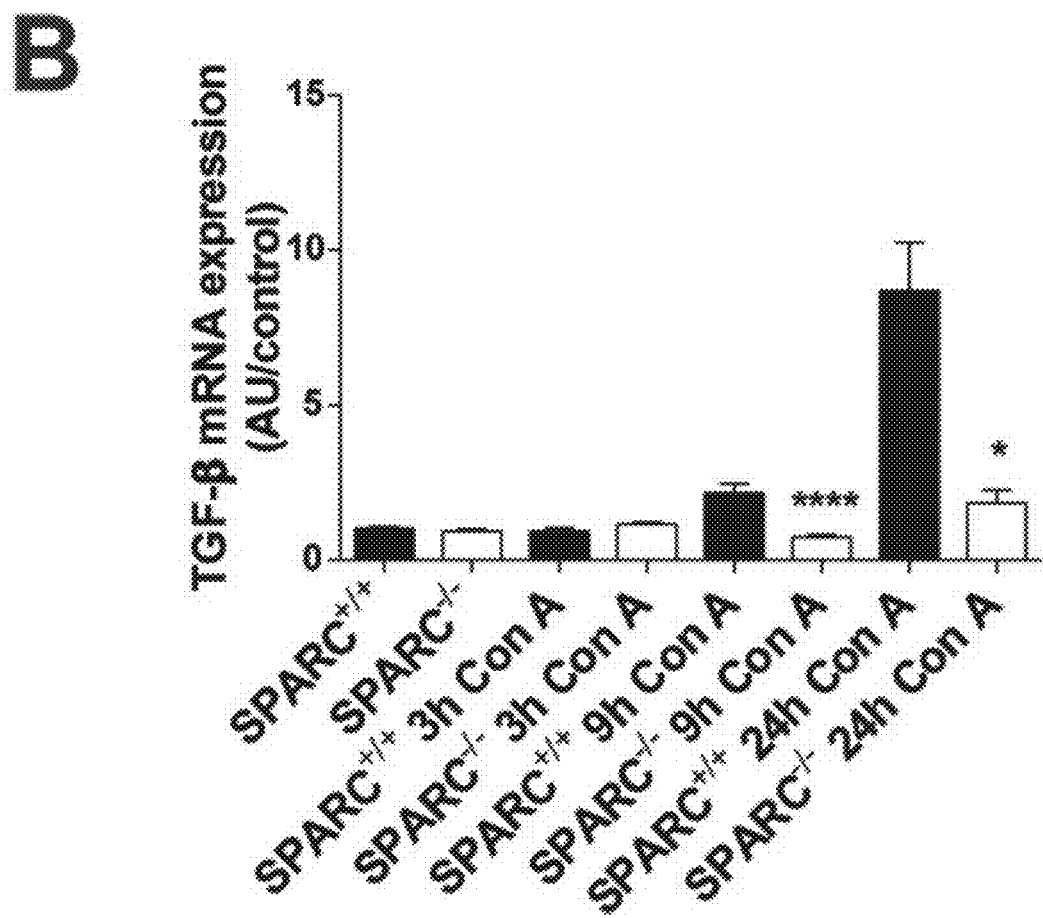
Figure 7:
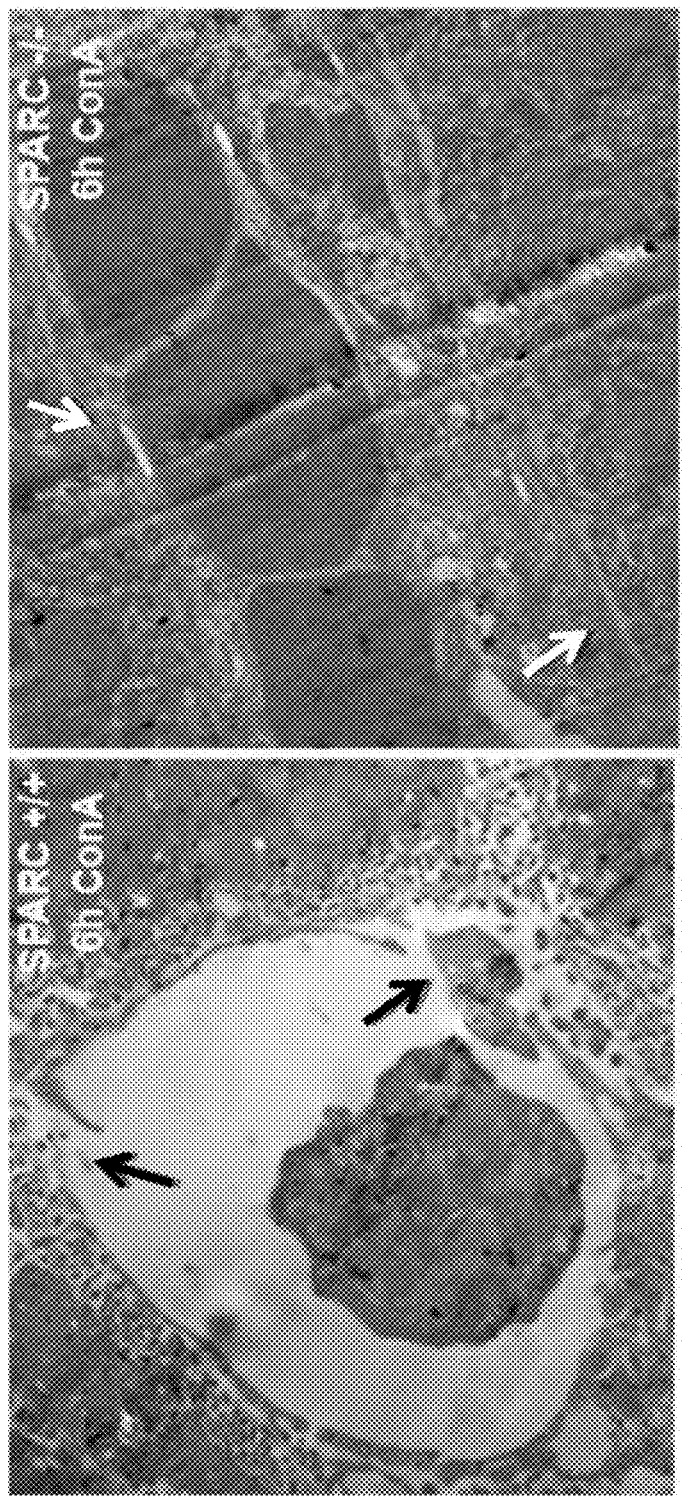
FIG. 7. Endothelial cell layer was preserved in SPARC deficient mice. Electron microscopy micrograph of liver tissue from SPARC$^{+/+}$ mice (left panel) or SPARC$^{-/-}$ (right panel) treated with ConA for 6 h. Note the loss of continuity of the endothelial cell layer in SPARC$^{+/+}$ mice, contrary to what happens in SPARC$^{-/-}$.

SPARC was overexpressed 24 h after ConA, anti-CD95 or Galactosamine/LPS administration (FIG. 1A). Immunohistochemistry analysis of ConA-treated mice revealed that SPARC was mainly expressed in sinusoid areas (FIG. 1B). Histological analyses of liver tissue sections indicated that $SPARC^{-/-}$ are significantly less sensitive to ConA-induced hepatic damage. Liver tissue obtained from $SPARC^{-/-}$ mice showed small areas of necrosis. In contrast, liver tissue sections form $SPARC^{+/+}$ treated mice presented extensive areas of necrosis (FIG. 2). $SPARC^{+/+}$ treated mice tissue showed an increased infiltration of CD4+ and CD8+ T cell within the liver lobules and around the central veins and portal tracts, indicating the ongoing inflammatory process (FIG. 3). Consistently, serum AST and ALT levels after ConA injection were significantly lower in $SPARC^{-/-}$ compared to $SPARC^{+/+}$ mice (FIG. 4). TUNEL staining showed more severe apoptosis in $SPARC^{+/+}$ (FIG. 5). Serum concentration of pro-inflammatory cytokines, IL-6 and TNF-α, were significantly reduced in $SPARC^{-/-}$ mice at 3 and 9 h after ConA application (FIG. 6A). A significant decrease in the TGF-β expression was found in $SPARC^{-/-}$ mice when compared to $SPARC^{+/+}$ after 9 h and 24 h of ConA administration (FIG. 6B). Finally ConA-treated $SPARC^{-/-}$ mice showed preservation of sinusoidal endothelial barrier that was clearly damaged in $SPARC^{+/+}$ mice (FIG. 7).

Figure 8:
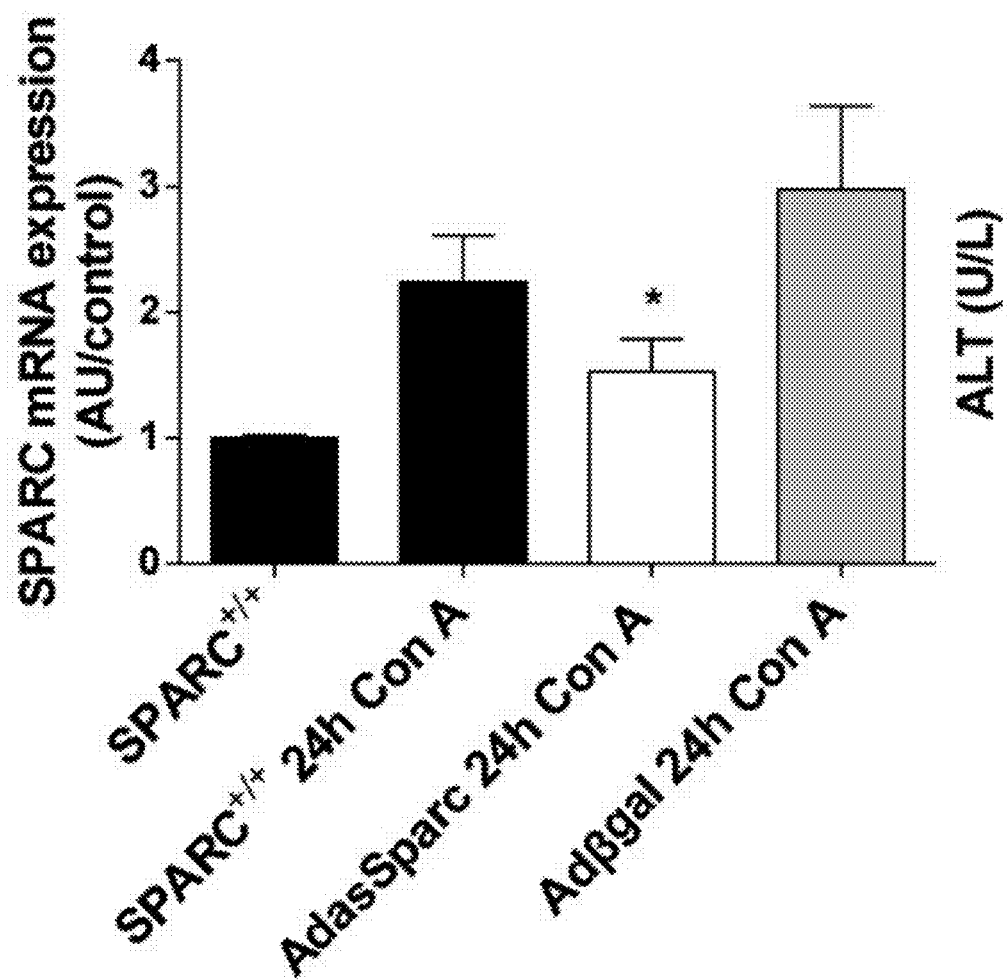
FIGS. 8A-8B. Preventive effect of AdasSPARC and therapeutic effect of siSPARC. (A) qPCR analyses of liver samples from untreated wt, ConA-treated SPARC$^{+/+}$, Adβgal ConA-treated SPARC$^{+/+}$, or AdasSPARC SPARC$^{+/+}$ mice. *p<0.05 vs. Adβgal SPARC$^{+/+}$ 24 h ConA, Dunn's multiple test. Serum AST and ALT levels were measured after 24 h between ConA-treated SPARC$^{+/+}$, AdasSPARC SPARC$^{+/+}$ and Adβgal SPARC$^{+/+}$ groups. p<0.05 vs. Adβgal SPARC$^{+/+}$ 24 h ConA, Dunn's multiple test. H&E microphotographs of liver sections from ConA-treated SPARC$^{+/+}$, AdasSPARC SPARC$^{+/+}$ and Adβgal SPARC$^{+/+}$ mice stained with H&E are also showed (200×). (B) qPCR analyses of liver samples from untreated wt, siControl ConA-treated SPARC$^{+/+}$, or siSPARC SPARC$^{+/+}$ mice. *p<0.01 vs. siControl ConA, Dunn's multiple test. Serum AST levels were measured after 48 h on siControl SPARC$^{+/+}$ and siSPARC SPARC$^{+/+}$ mice. p<0.05 vs. SPARC$^{+/+}$ 24 h ConA, Dunn's multiple test. Survival curves of sham, vehicle ConA, siControl ConA-treated SPARC$^{+/+}$, or siSPARC SPARC$^{+/+}$ mice. p<0.05, Log-rank test.
Figure 8:
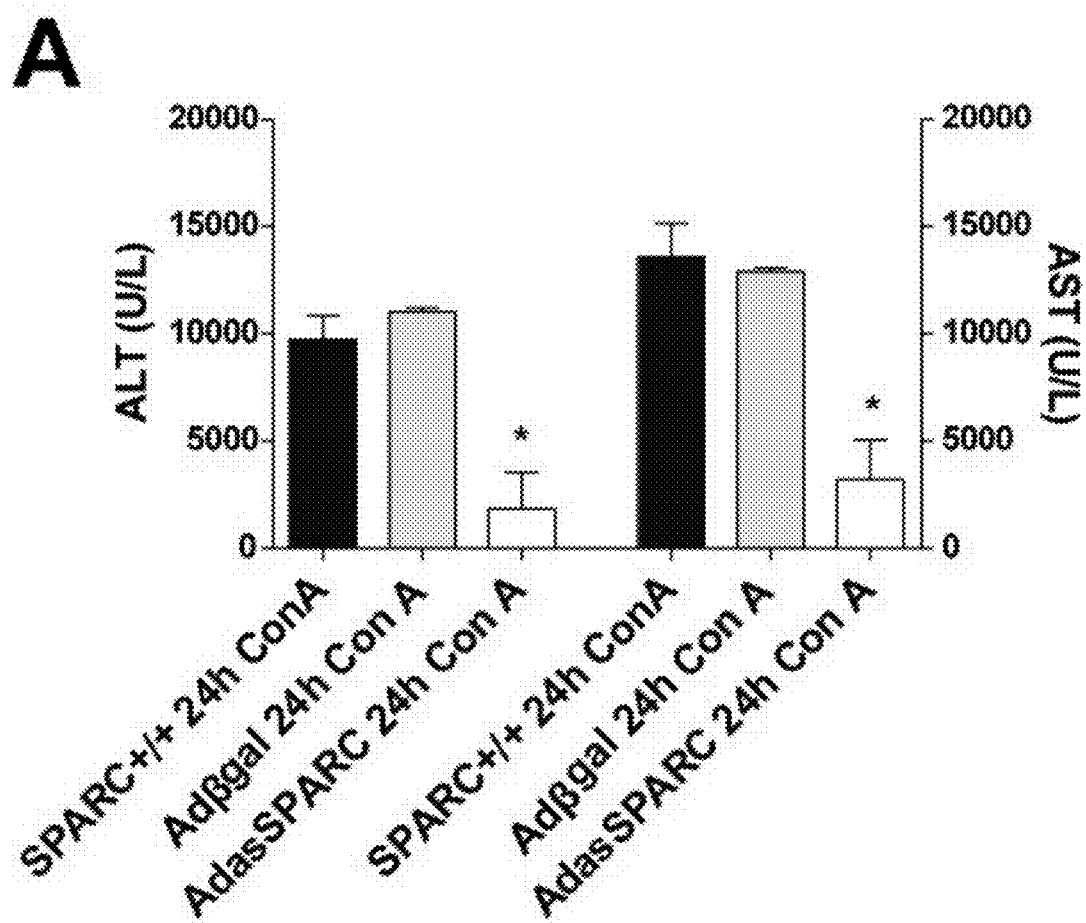
Figure 8:
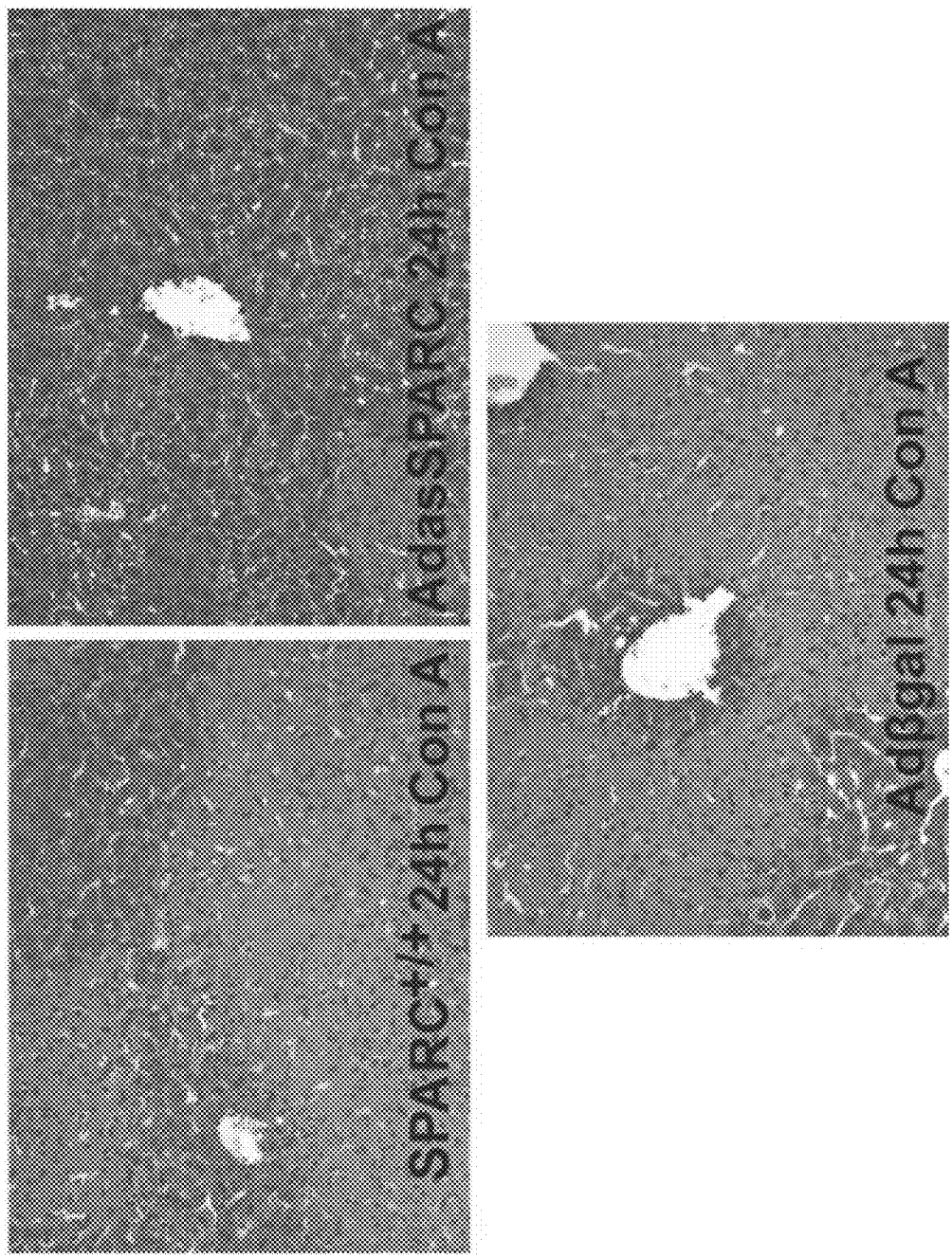
Figure 8:
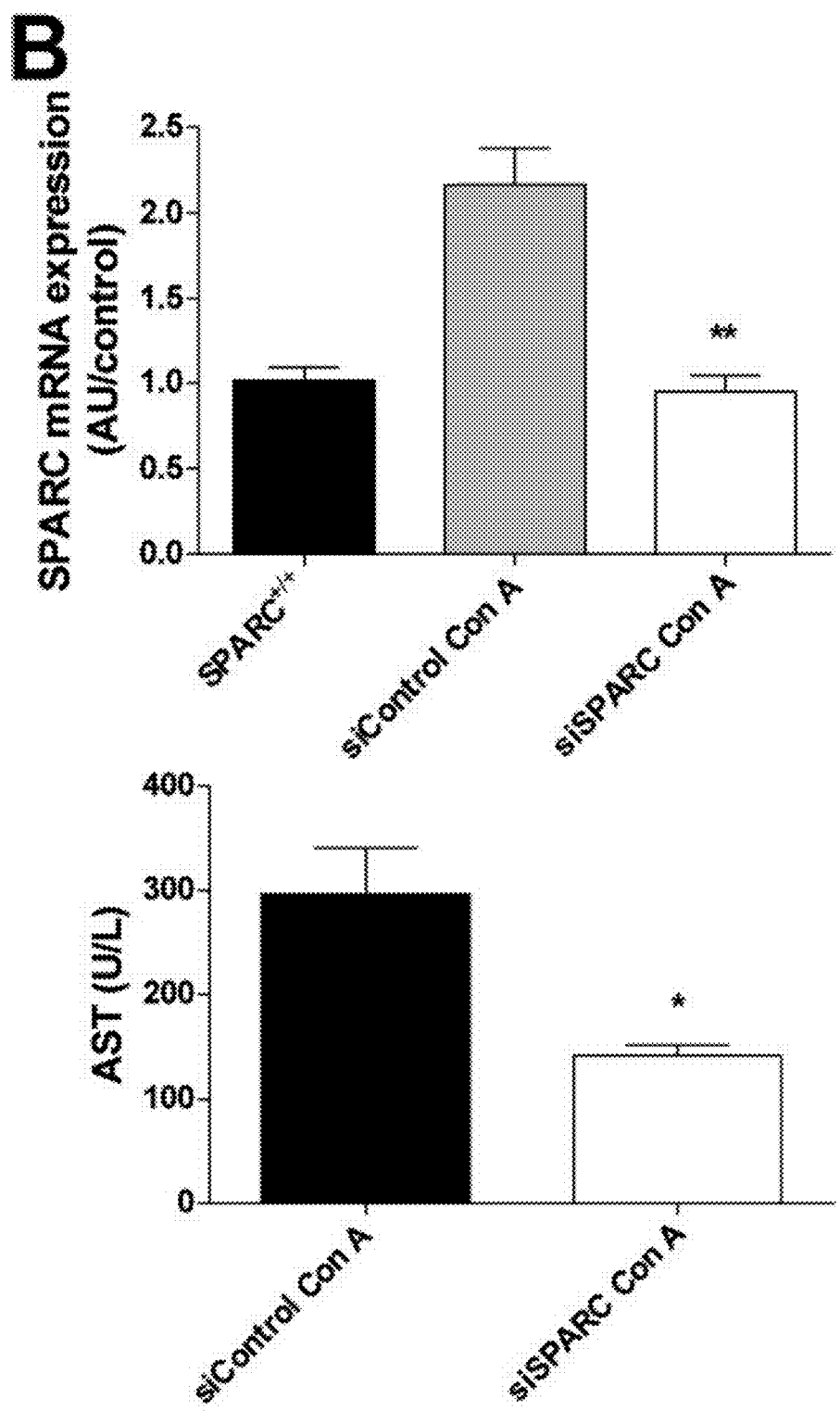
Figure 8:
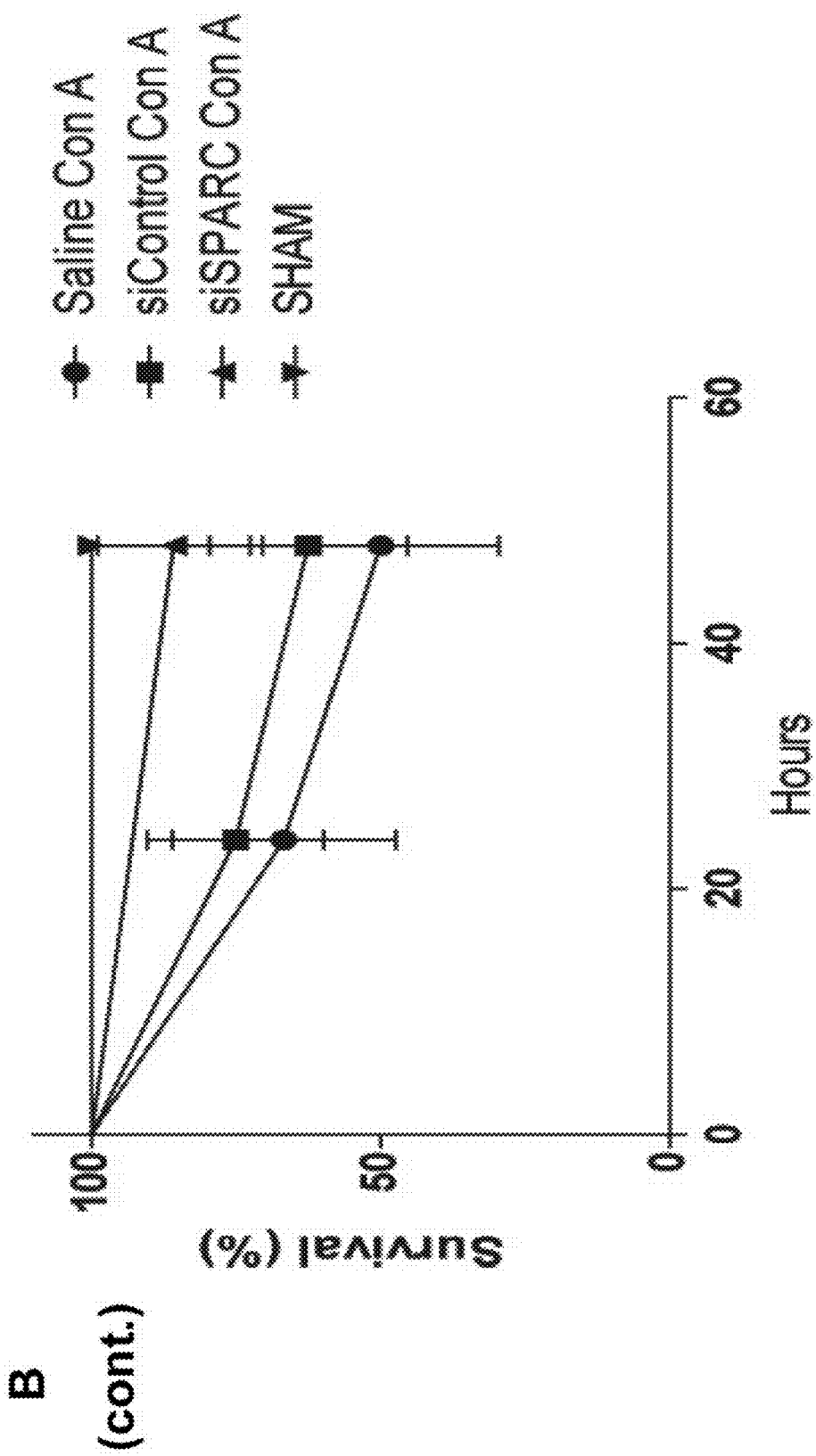

Then we used a gene therapy tool in order to prevent the development of acute hepatitis by the injection of an adenovirus encoding for a SPARC mRNA antisense sequence (AdasSPARC) 2 days before the injury with ConA (FIG. 8). SPARC expression was significantly reduced by AdasS- PARC. Animals with SPARC knock-down induced showed a decreased level of transaminases and a reduced liver damage (FIG. 8A).

To further evaluate the therapeutic effect of SPARC inhibition once liver injury was induced, small interference RNA anti-SPARC (siSPARC) was administered via portal vein 2 hrs after ConA injection. Forty eight hours after siSPARC injection siSPARC was able to attenuate hepatic SPARC expression as shown by qPCR. A decrease in liver damage by AST analysis was observed in comparison with siControl and, most important, therapeutic inhibition of SPARC resulted in prolonged animal survival (FIG. 8B).

Figure 9:
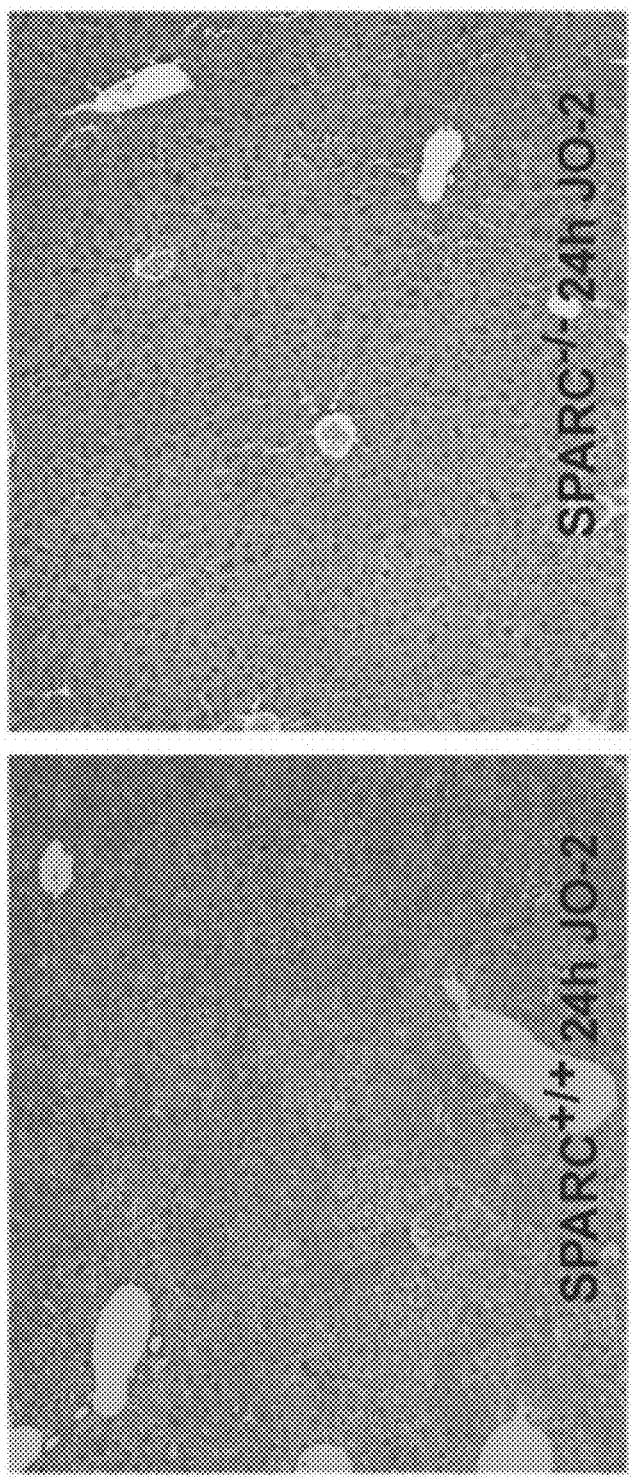
FIGS. 9A-9B. Reduced Jo2-Induced Hepatitis in SPARC knockout mice. (A) Representative photomicrographs of liver sections stained with H&E from 24 h ConA-treated SPARC$^{+/+}$ or SPARC$^{-/-}$ mice. Original magnification 40×. (B) Transaminases levels.
Figure 9:
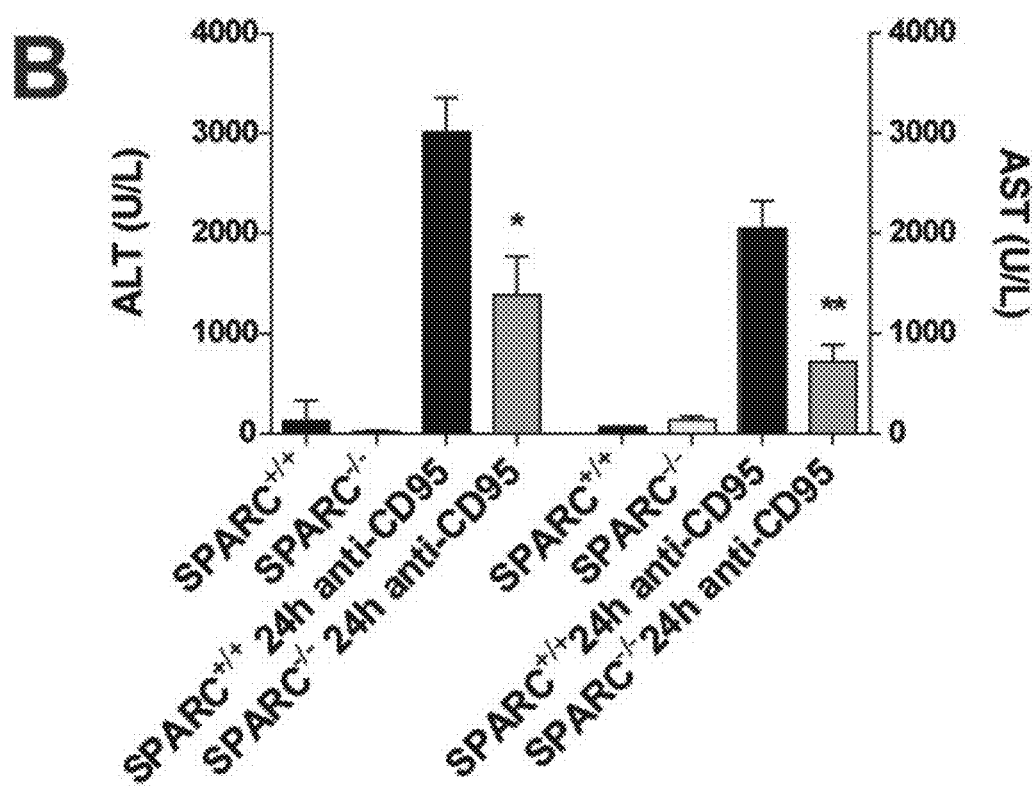

Similar results were observed in another model of acute liver failure mediated by the immune system. An agonistic antibody against Fas (Jo-2) was intraperitoneal injected to SPARC$^{+/+}$ or SPARC$^{-/-}$ mice. When SPARC$^{+/+}$ mice were treated with Jo-2 they showed extensive areas of liver necrosis and elevated levels of transaminases. On the contrary, in SPARC$^{-/-}$ animals the amount of liver damaged decreased significantly (FIG. 9).

These results confirmed the observation that SPARC knockdown exerts a protective effect against immune-mediated acute liver damage.

Figure 10:
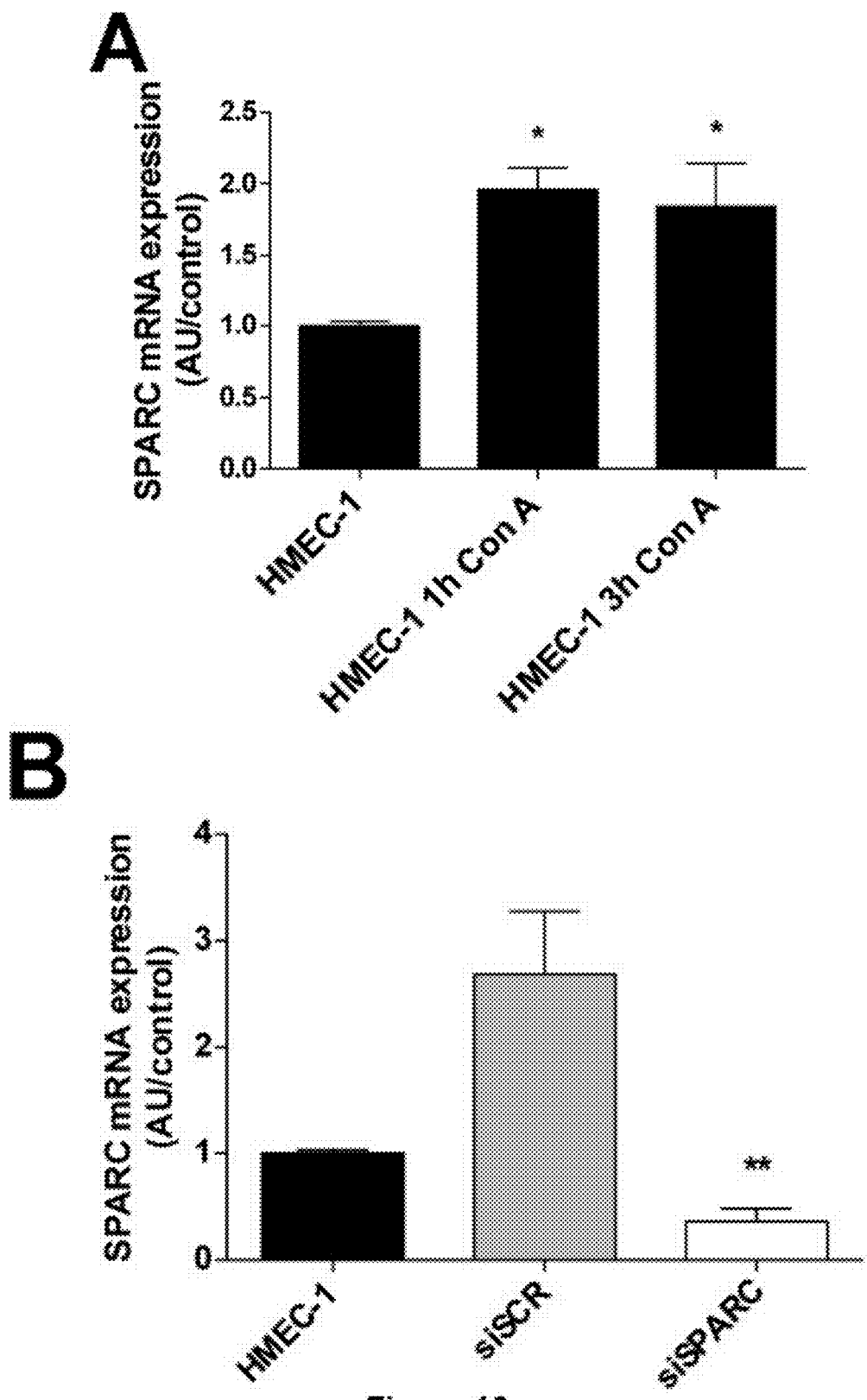
FIGS. 10A-10E. Reduced alterations in endothelial cells after SPARC knockdown. (A, B) qPCR for SPARC expression on HMEC-1 cells. *p<0.05, HMEC-1 1 h and 3 h ConA versus untreated cells, Dunn's multiple test. p<0.01, siSPARC vs. siSCR, Mann Whitney test. (C) Phalloidin staining of HMEC cells. (D) Apoptosis quantification of HMEC-1 cells by ConA incubation, using the AO/EB assay. p<0.01 HMEC-1 vs. HMEC-1 1 h ConA; ****p<0.0001 HMEC-1 vs. HMEC-1 3 h ConA; °p<0.05, siSCR 3 h ConA vs. siSPARC 3 h ConA, Mann Whitney test. (E) Splenocytes-HMEC-1 layer transmigration assay. Mean values±SEM for individual groups are shown. *p<0.05 HMEC-1 vs. HMEC-1 3 h ConA, σσσp<0.01 siSCR 3 h ConA vs. siSPARC 3 h ConA, Dunn's multiple test.
Figure 10:
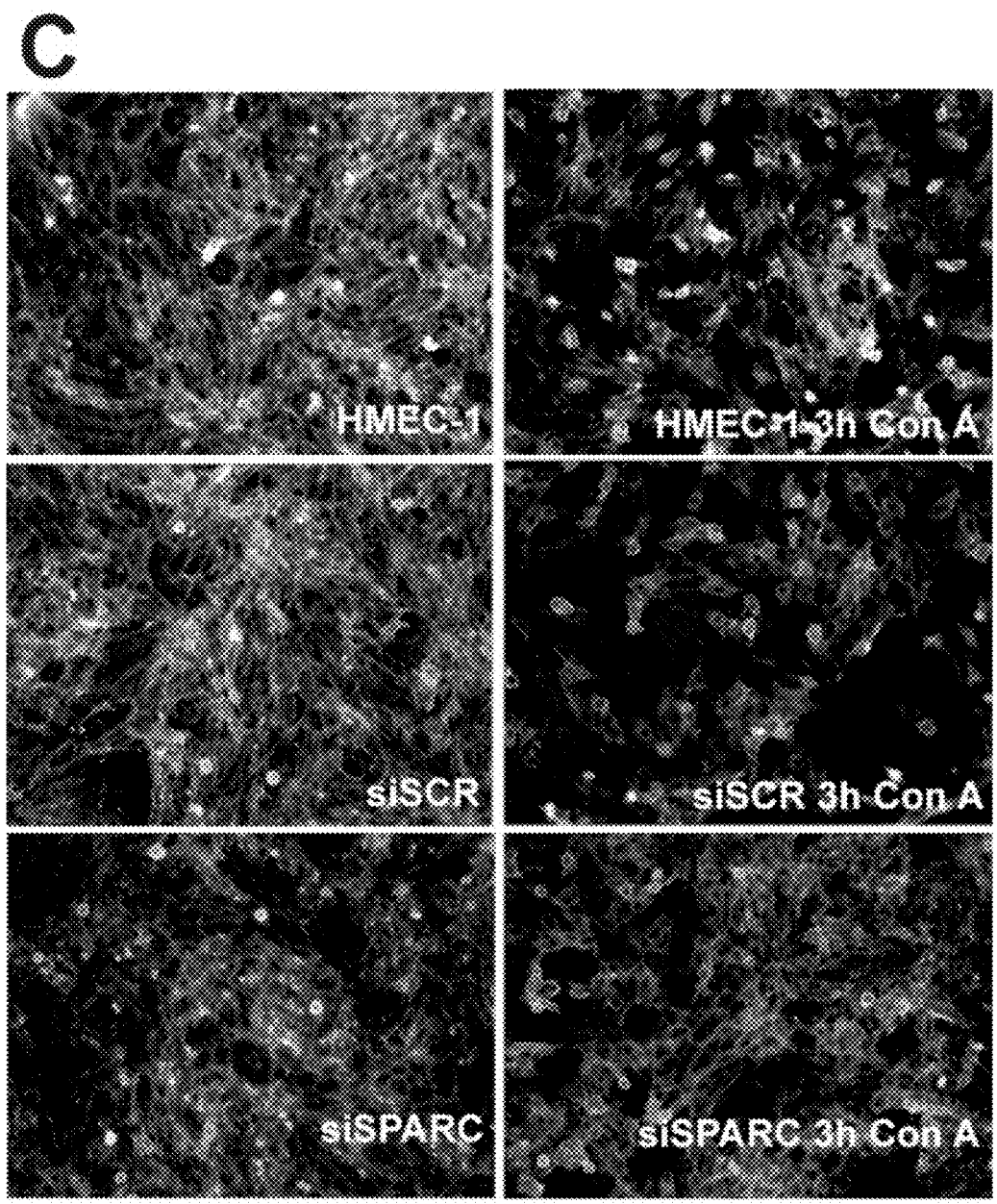
Figure 10:
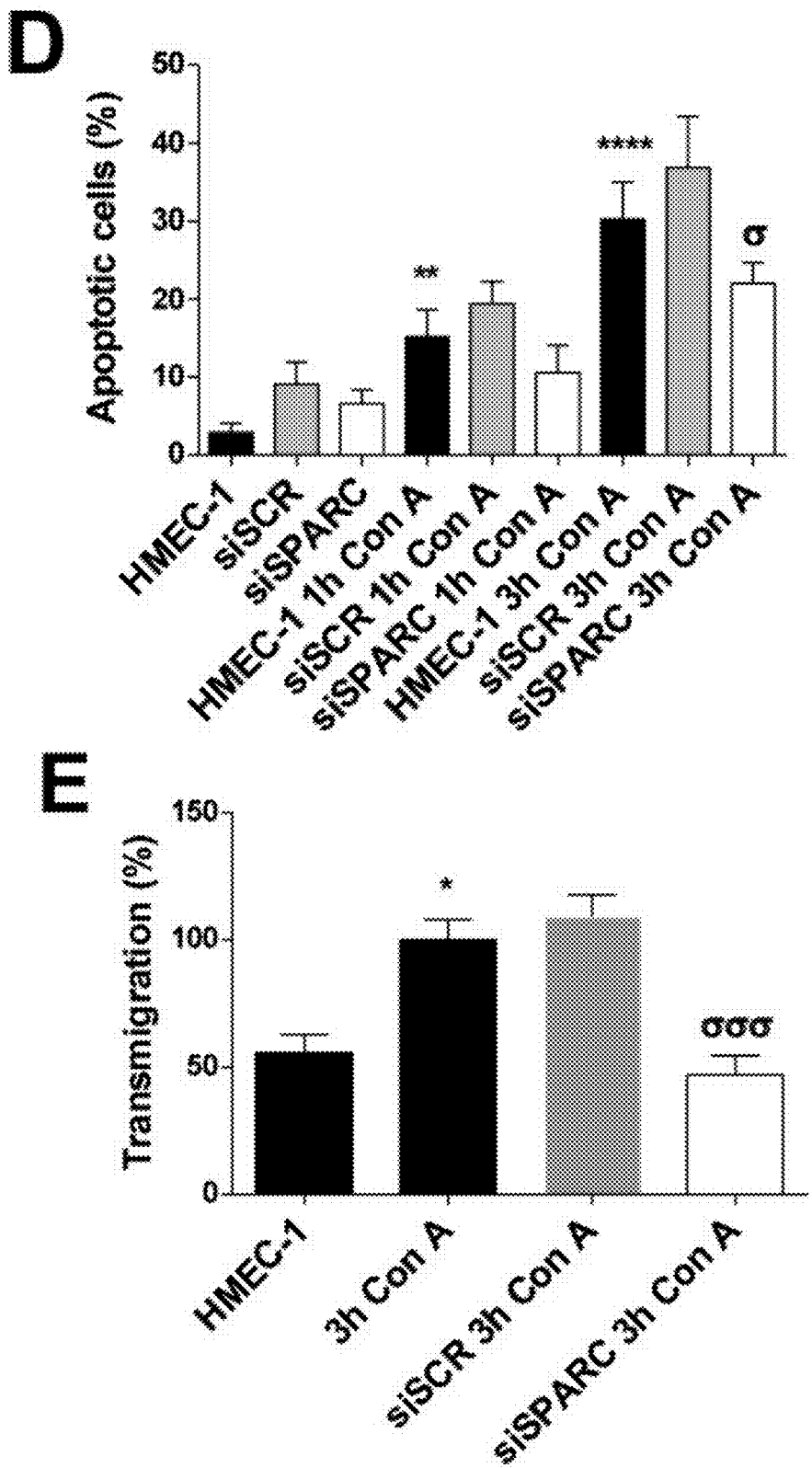

Alterations in liver sinusoidal endothelial cells (LSECs) are likely among the earliest events of severe liver injury facilitating infiltration of activated T-cells into liver parenchyma. As observed by electron microscopy LSEC layer was disrupted in SPARC$^{+/+}$ mice after ConA administration. In culture experiments with HMEC-1 cells we showed an induction in SPARC mRNA expression after 1 h of in vitro ConA incubation (FIG. 10A). To assess the role of SPARC deficiency in endothelial cells, SPARC was knocked-down by using a lentivirus encoding a siRNA specific for SPARC (FIG. 10B). A significant reduction in both the proportion of adhered cells with a thick fibrillar pattern, known as stress fibers and in the phalloidin staining distribution as well as an increased in gaps separating cells were found in cultures of naive and siSCR-treated cells when compared to SPARC siRNA-treated cells (FIG. 10C). Interestingly, SPARC knockdown resulted in a significant reduction in the percentage of apoptotic cells after 3 h of ConA incubation (FIG. 10D). We assessed if SPARC knockdown decreases the amount of transmigrated lymphocytes through ConA-treated HMEC-1 cell layer towards CCL19 and CCL21 as chemoattractants.

SPARC inhibition resulted in a reduction in the number of lymphocytes that migrated across the endothelial cell monolayer (FIG. 10E). These data suggest that SPARC inhibition might protect endothelial cell layer from apoptosis induction caused by ConA and preserve endothelial cell monolayer.

Figure 11:
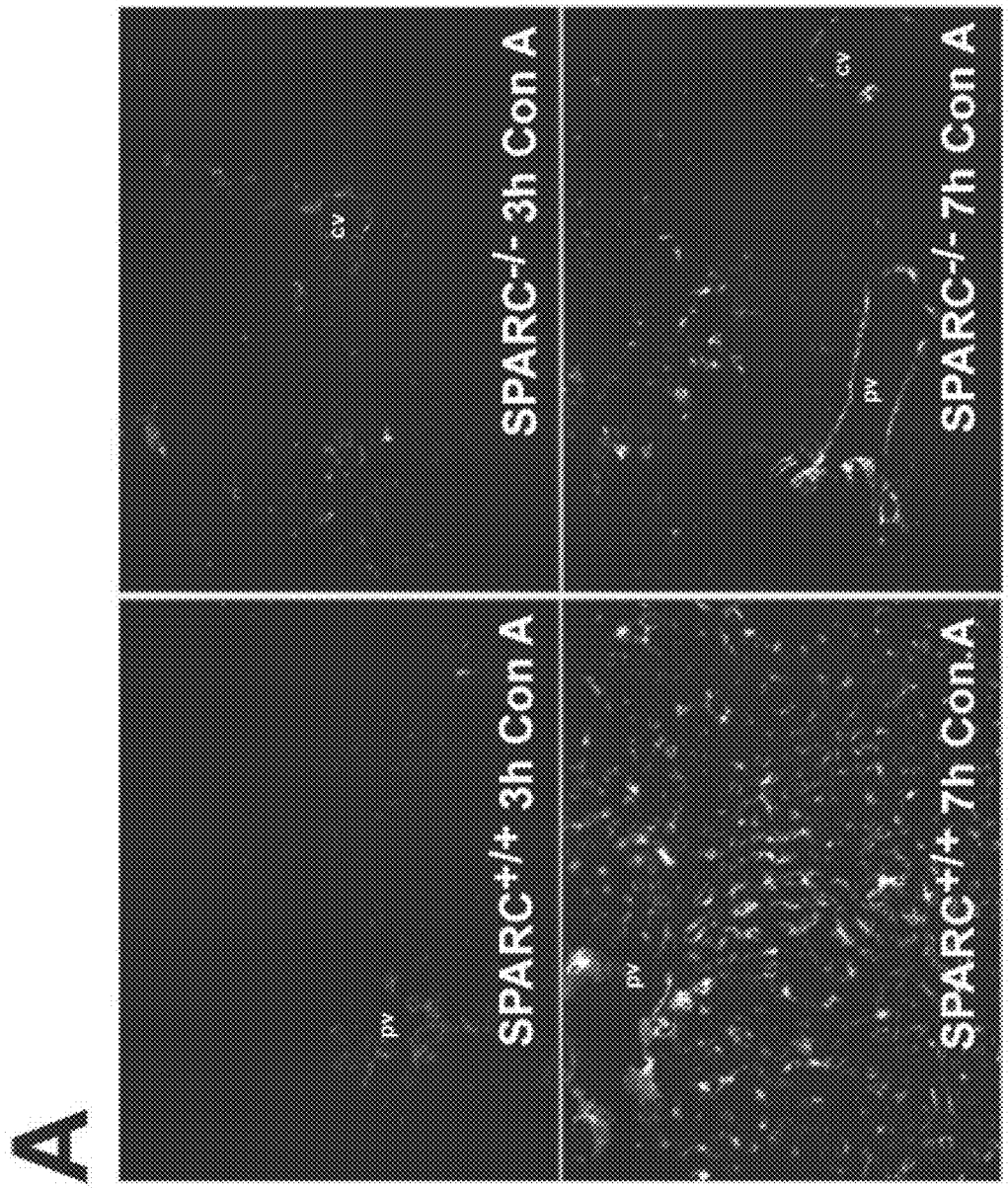
FIGS. 11A-11B. Immunofluorescence for VCAM-1 (200×). pv, portal vein; cv, central vein. **p<0.01 SPARC$^{+/+}$ 7 h ConA vs. SPARC$^{-/-}$ 7 h ConA, Dunn's multiple test.
Figure 11:
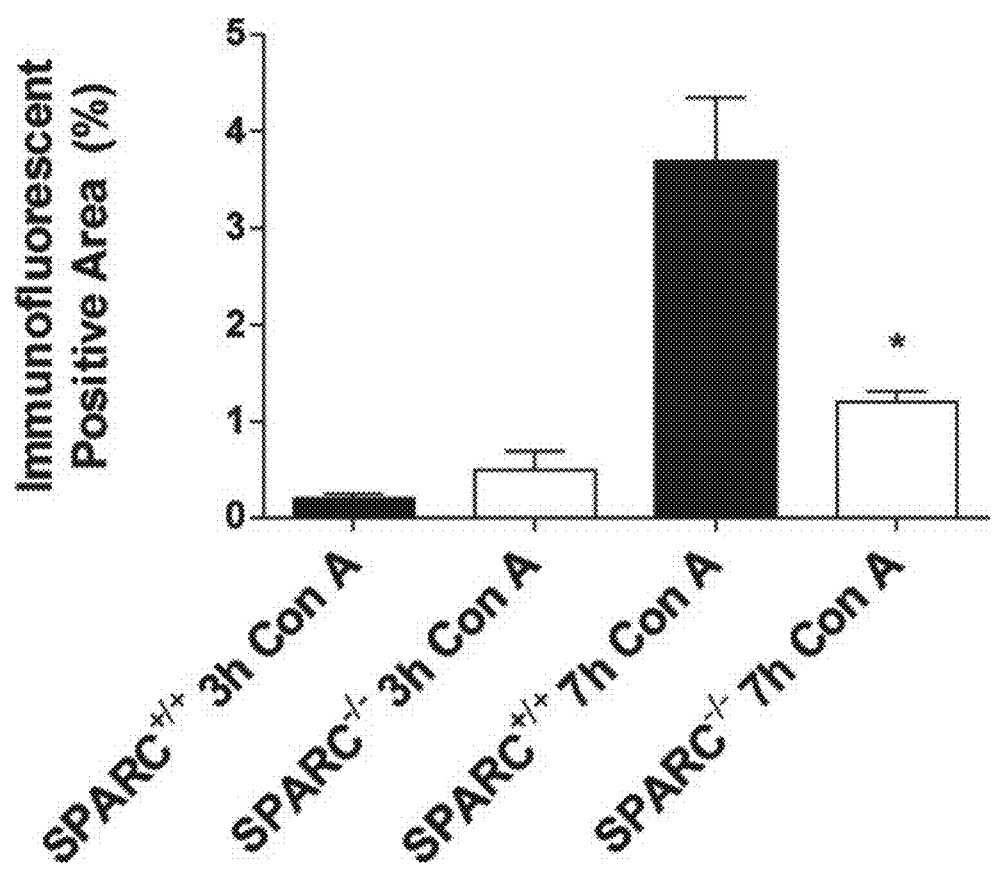

A marked upregulation of VCAM-1, an endothelial molecule induced by inflammation, was found in the liver of wild-type mice at 7 h after ConA application, which was markedly blunted in SPARC$^{-/-}$ mice (FIG. 11). These results further suggest the involvement of SPARC in sinusoidal cells inflammation in early development of severe liver injury.

Figure 12:
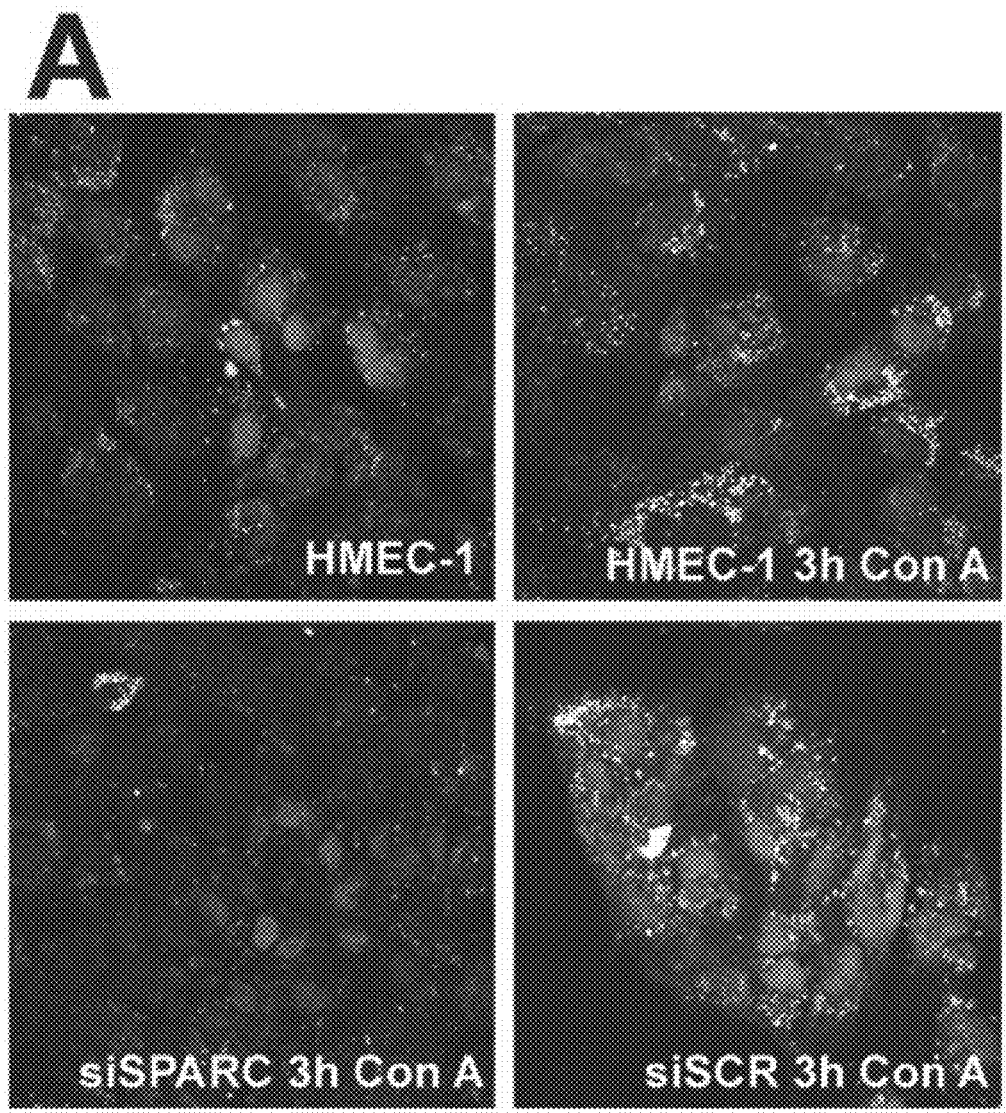
FIGS. 12A-12B. LC3 dots per HMEC-1 cell (600×); **p<0.01, HMEC-1 vs. 3 h ConA, siSCR 3 h ConA vs. siSPARC 3 h ConA; *p<0.05, HMEC-1 chloroquine vs. 3 h ConA chloroquine, siSCR 3 h ConA chloroquine vs. siSPARC 3 h ConA chloroquine, Dunn's multiple comparisons test.
Figure 12:
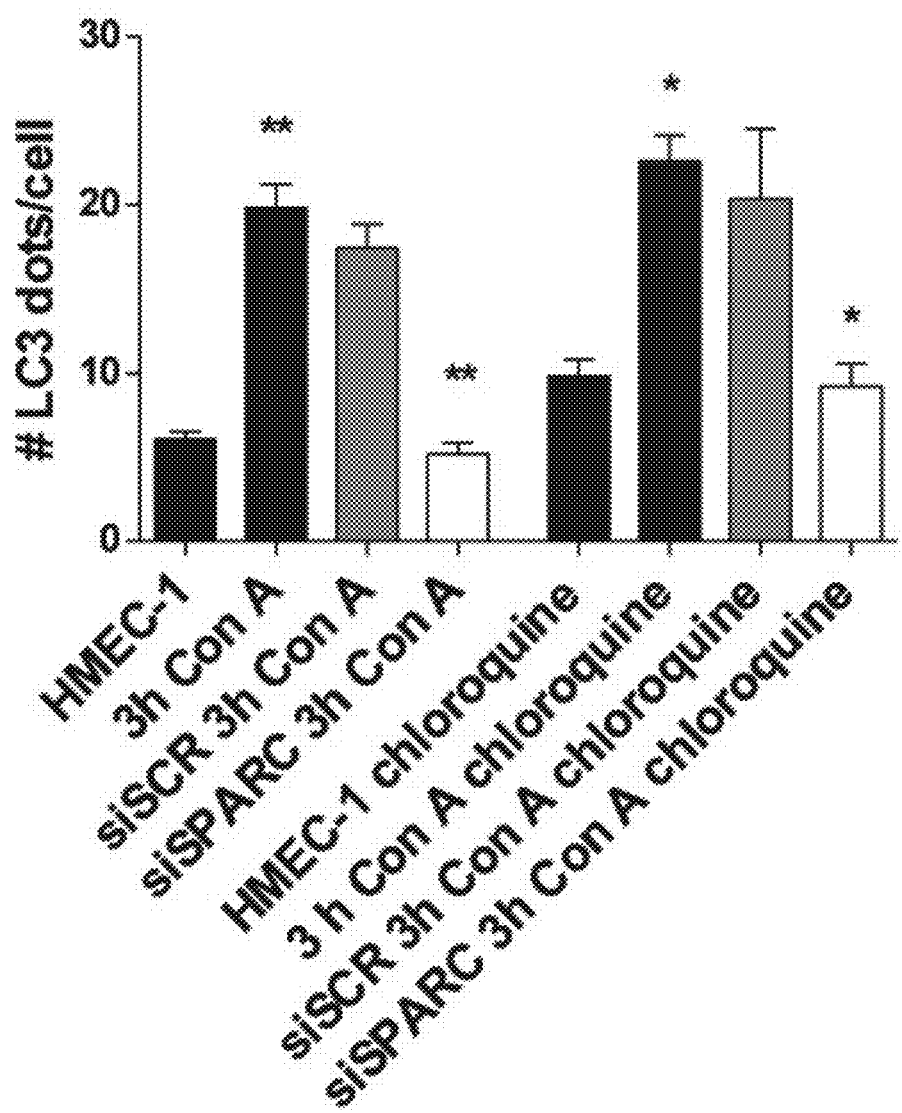

To further understand how the endothelial layer could be affected by ConA resulting in subsequent hemorrhage and massive cellular infiltration, HMEC-1 cells were stained with the autophagic marker LC3. LC3 punctate pattern was increased in HMEC-1 cells after 3 h of ConA incubation. SPARC knockdown prevented LC3 staining. Blocking autophagy using chloroquine confirmed that LC3 decrease with SPARC knockdown resulted from autophagy inhibition since LC3 dots remained stable and not accumulated when SPARC was attenuated and the LC3 flux interrupted (FIG. 12). These results indicate that ConA induces autophagy in endothelial cells, which is partially mediated by SPARC.

Figure 13:
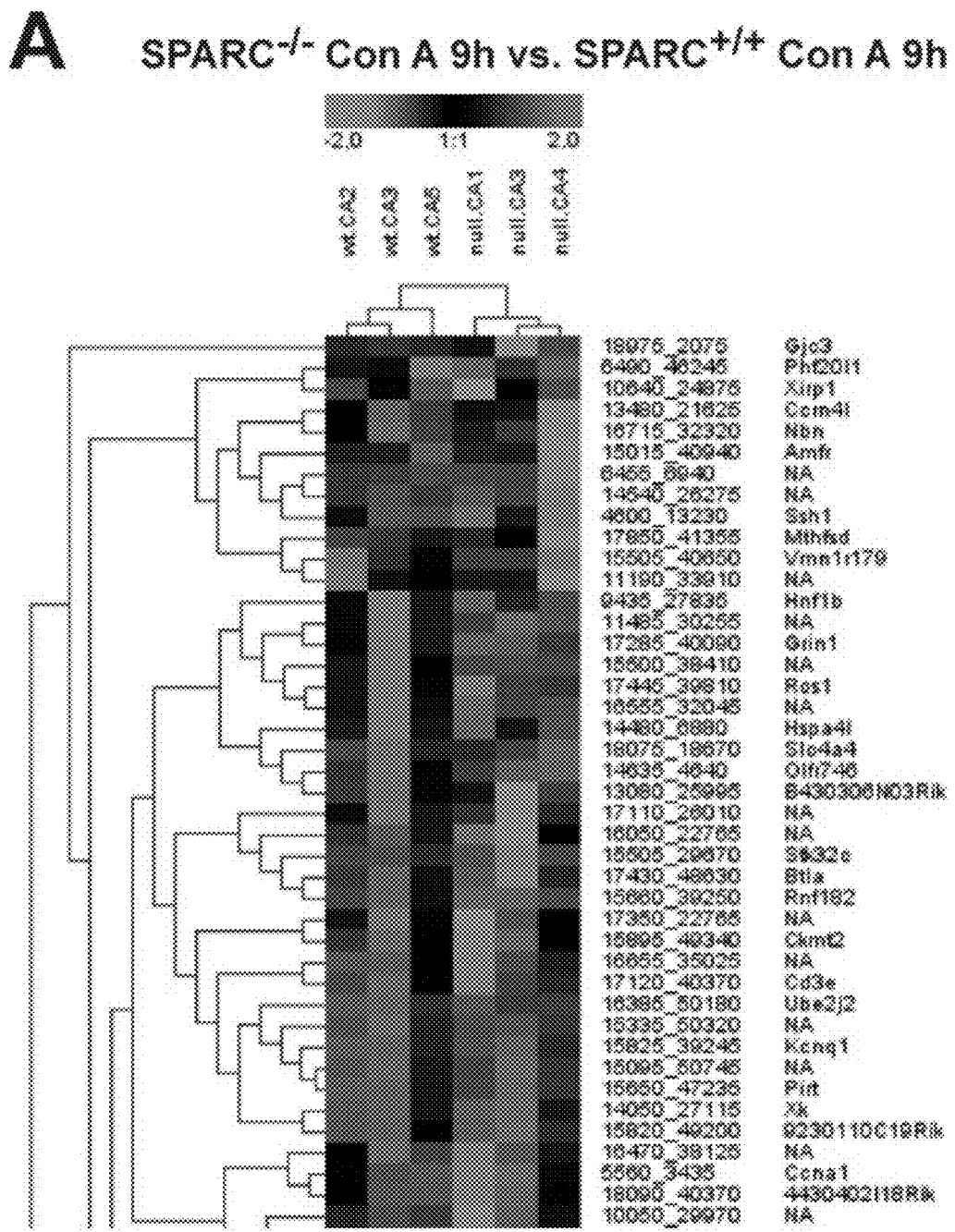
FIGS. 13A-13C: Heatmap and top network of differentially expressed genes. (A) Heatmap of differential gene expression among experimental groups at 9 h after ConA application. (B) Top network of differentially expressed genes in between SPARC$^{-/-}$ and SPARC$^{+/+}$ after 9 h of ConA treatment, as identified by IPA analysis. Up-regulated and down-regulated genes in SPARC$^{-/-}$ mice are shown in different shades of gray, respectively. Intensity of the color shows the level of gene expression. (C) CAPBZ mRNA expression vs. SPARC$^{+/+}$ and SPARC$^{-/-}$ 9 h ConA.
Figure 13:
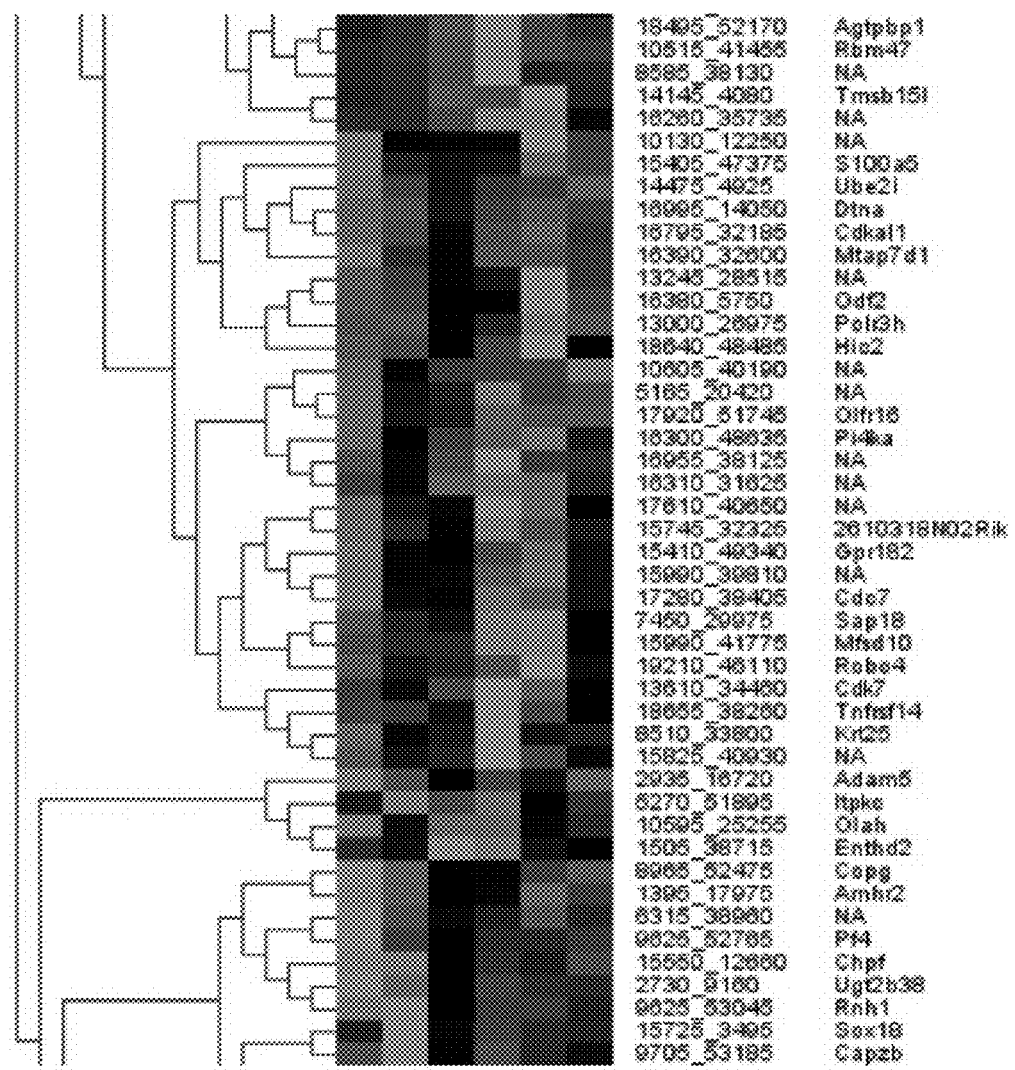
Figure 13:
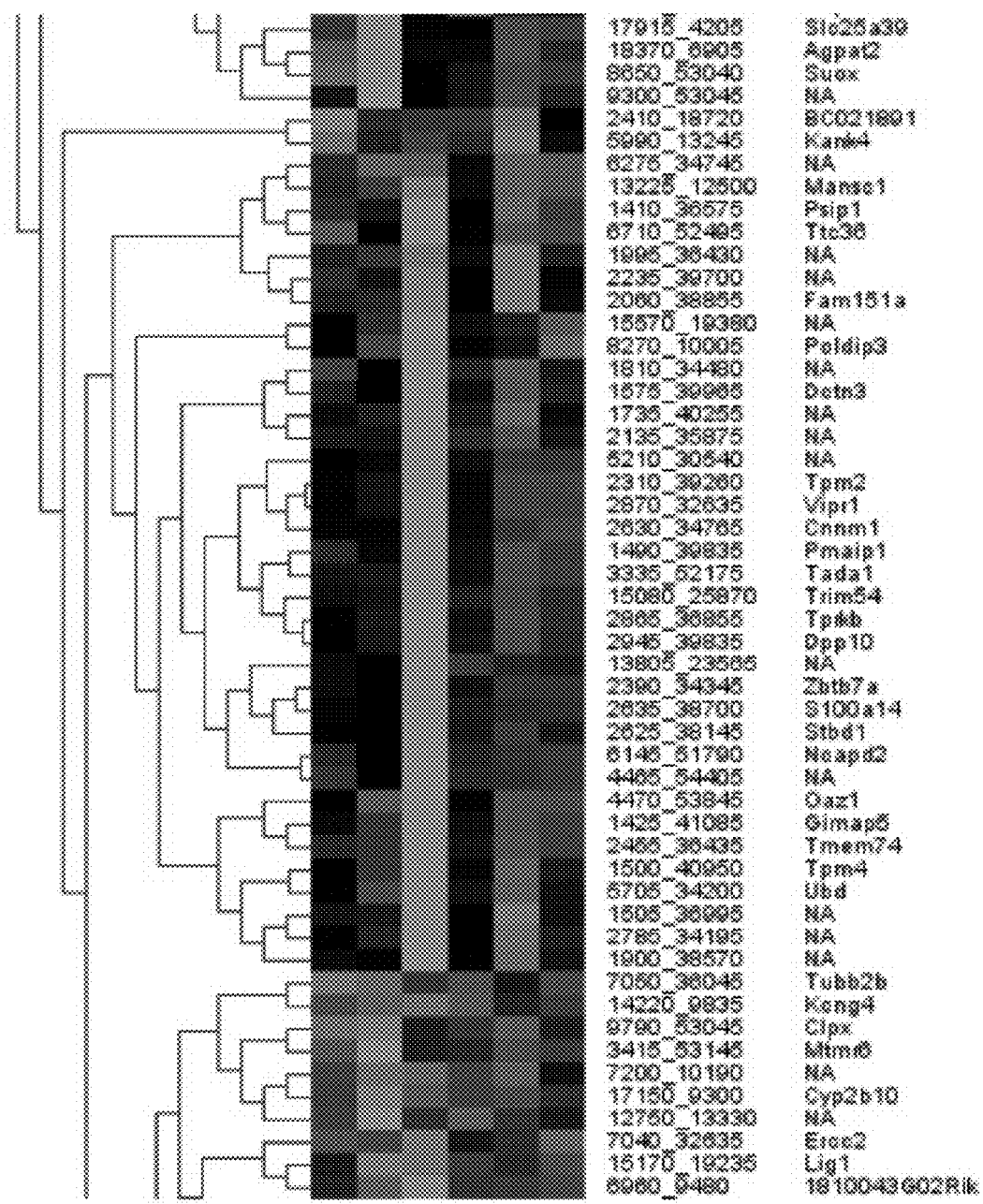
Figure 13:
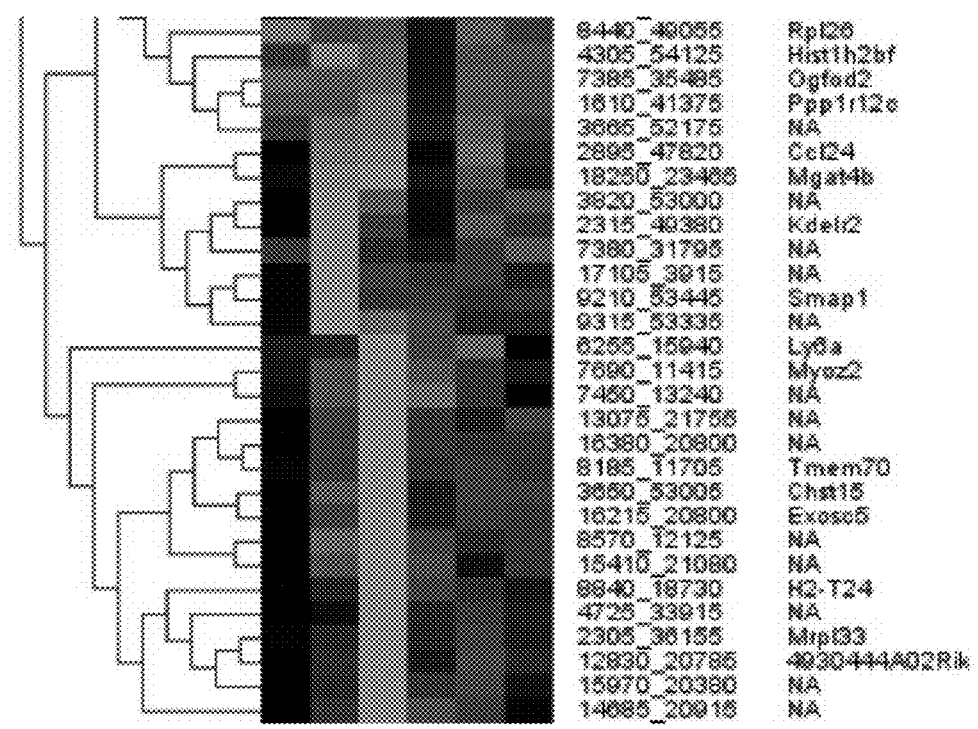
Figure 13:
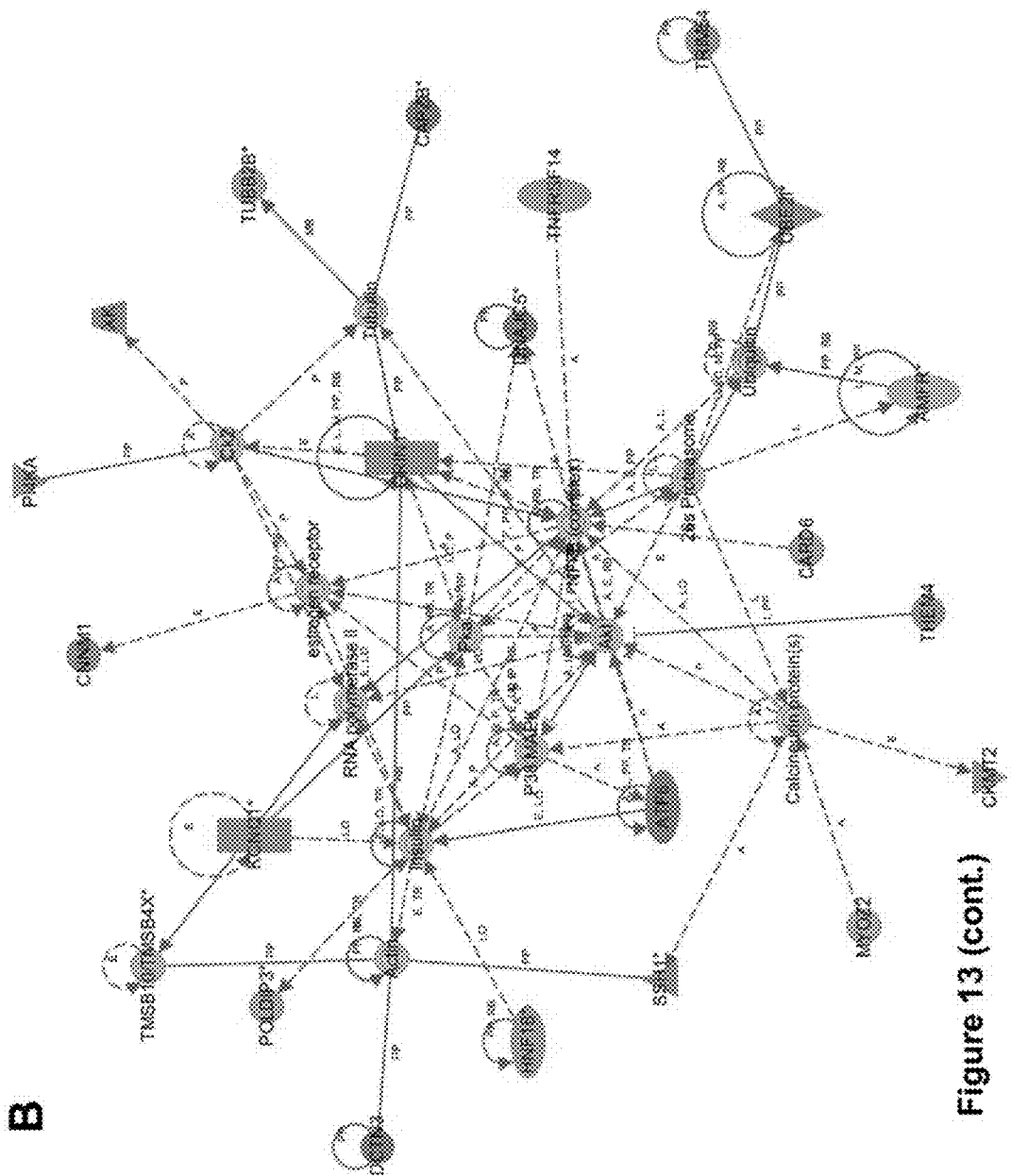
Figure 13:
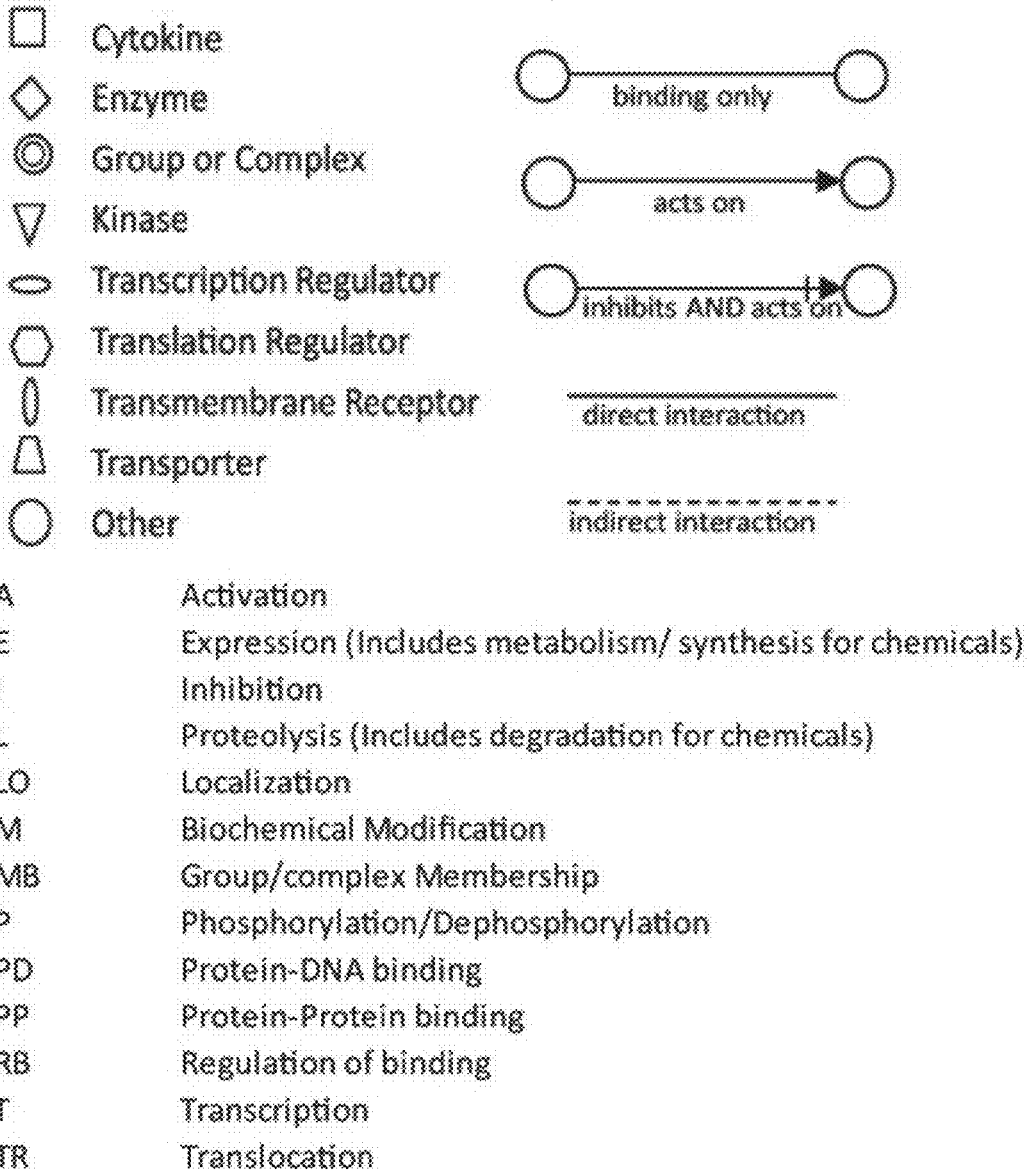
Figure 13:
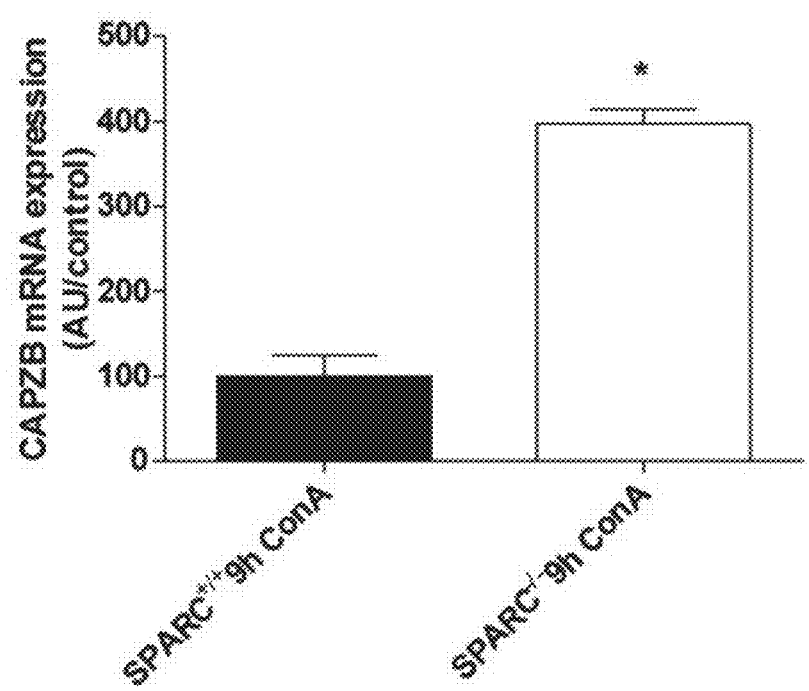
Figure 13:
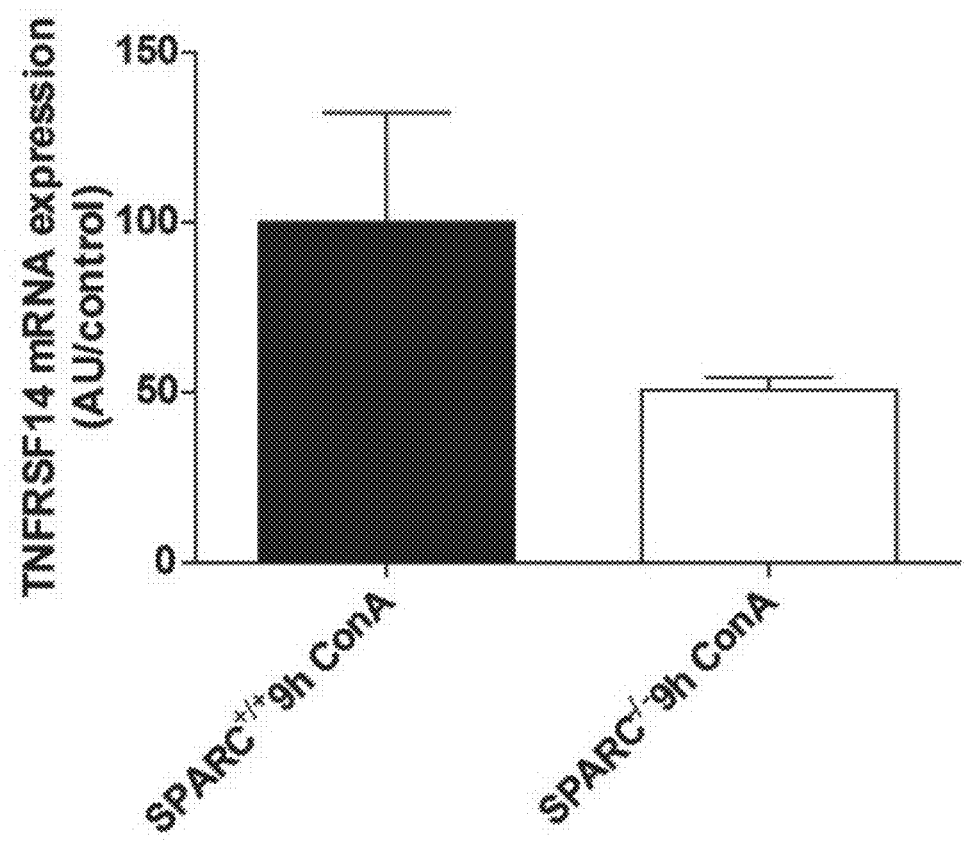

Transcriptome analysis reveals molecular mechanisms potentially involved in the role of SPARC in ConA-induced severe liver damage (FIG. 13). Microarray analysis was performed in liver tissue from SPARC$^{-/-}$ and SPARC$^{+/+}$ mice at 9 h after ConA administration. A total of 169 genes showed changes (p<0.01; 94 upregulated and 75 downregulated genes) in SPARC$^{-/-}$ mice when compared to wt. A list of the significantly modified genes as classified by ontological biological process categories was generated. Interestingly, canonical pathways and biological functions identified by IPA showed key groups of genes associated with cell adhesion, cytoskeletal organization, and apoptosis (FIG. 13). They include upregulation of actin capping protein β2 (CAPZB, NM_009798) gene, tubulin β Class IIb (TUBB2B, NM_023716), and down-regulation of thymosin β (TMSB10, NM_001190327), slingshot homolog 1 (SSH1, NM_198109), thioesterase superfamily member 4 (THEM4, NM_029431), tumor necrosis factor receptor superfamily member 14 (TNFRSF14, NM_178931) and potassium voltage-gated channel, KQT-Like subfamily member 1 (KCNQ1, NM_008434).

REFERENCES

Atorrasagasti C, Aquino J B, Hofman L, Alaniz L, Malvicini M, Garcia M et al. SPARC downregulation attenuates the profibrogenic response of hepatic stellate cells induced by TGF-beta1 and PDGF. American journal of physiology. Gastrointestinal and liver physiology 2011; 300(5): G739-48.

Barker, T. H., Baneyx, G., Cardo-Vila, M., Workman, G. A., Weaver, M., Menon, P. M., Dedhar, S., Rempel, S. A., Arap, W., Pasqualini, R., Vogel, V. & Sage, E. H. (2005). Sparc Regulates Extracellular Matrix Organization Through Its Modulation Of Integrin-Linked Kinase Activity. J Biol Chem 280(43): 36483-36493.

Bernuau, J. & Benhamou, J. (1999). Fulminant And Subfulminant Hepatic Failure. Oxford Textbook Of Clinical Hepatology 2: 923-942.

Bradshaw, A. D. and E. H. Sage (2001). "SPARC, a matricellular protein that functions in cellular differentiation and tissue response to injury." J Clin Invest 107(9): 1049-1054.

Brekken, R. A. and E. H. Sage (2000). "SPARC, a matricellular protein: at the crossroads of cell-matrix." Matrix Biol 19(7): 569-580.

Camino, A. M., C. Atorrasagasti, et al. (2008). "Adenovirus-mediated inhibition of SPARC attenuates liver fibrosis in rats." J Gene Med 10(9): 993-1004.

Francki, A., A. D. Bradshaw, et al. (1999). "SPARC regulates the expression of collagen type I and transforming growth factor-beta1 in mesangial cells." J Biol Chem 274(45): 32145-32152.

Lane, T. F. & Sage, E. H. (1994). The Biology OfSparc, A Protein That Modulates Cell-Matrix Interactions. Faseb J 8(2): 163-173.

Piccioni F, Malvicini M, Garcia M G, Rodriguez A, Atorrasagasti C, Kippes N et al. Antitumor effects of hyaluronic acid inhibitor 4-methylumbelliferone in an orthotopic hepatocellular carcinoma model in mice. Glycobiology 2012; 22(3): 400-10.

Vaquero, J. and A. T. Blei (2003). "Etiology and management of fulminant hepatic failure." Curr Gastroenterol Rep 5(1): 39-47.

Wang, J. C., S. Lai, et al. (2010). "Attenuation of fibrosis in vitro and in vivo with SPARC siRNA." Arthritis Res Ther 12(2): R60.

The invention claimed is:

1. A method for treating acute liver failure or acute liver damage, the method comprising administering to a subject in need thereof a siRNA or a combination of siRNA molecules that are specifically targeted to SPARC mRNA, or a genetic construct capable of expressing said siRNA molecules that are specifically targeted to SPARC mRNA.

2. The method of claim 1, wherein said genetic construct is a recombinant lentivirus.

3. The method of claim 2, wherein said lentivirus is capable of expressing the siRNA encoded by SEQ ID NO.: 3.

4. The method of claim 1, wherein the siRNA has a sequence selected from SEQ ID NO.: 4, SEQ ID NO.: 5, SEQ ID NO.: 6 and SEQ ID NO.: 7, combinations thereof.

5. The method of claim 1, where the inhibition of SPARC expression occurs in the liver.

* * * * *

SEQUENCE LISTING

<160> NUMBER OF SEQ ID NOS: 13

<210> SEQ ID NO 1
<211> LENGTH: 912
<212> TYPE: DNA
<213> ORGANISM: Homo sapiens

<400> SEQUENCE: 1

```
atgagggcct ggatcttctt tctcctttgc ctggccggga gggccttggc agcccctcag      60
caagaagccc tgcctgatga gacagaggtg gtggaagaaa ctgtggcaga ggtgactgag     120
gtatctgtgg gagctaatcc tgtccaggtg gaagtaggag aatttgatga tggtgcagag     180
gaaaccgaag aggaggtggt ggcggaaaat ccctgccaga accaccactg caaacacggc     240
aaggtgtgcg agctggatga gaacaacacc cccatgtgcg tgtgccagga ccccaccagc     300
tgcccagccc ccattggcga gtttgagaag gtgtgcagca atgacaacaa gaccttcgac     360
tcttcctgcc acttctttgc cacaaagtgc accctggagg gcaccaagaa gggccacaag     420
ctccacctgg actacatcgg gccttgcaaa tacatccccc cttgcctgga ctctgagctg     480
accgaattcc ccctgcgcat gcgggactgg ctcaagaacg tcctggtcac cctgtatgag     540
agggatgagg acaacaacct tctgactgag aagcagaagc tgcgggtgaa gaagatccat     600
gagaatgaga agcgcctgga ggcaggagac accccgtgg agctgctggc ccgggacttc     660
gagaagaact ataacatgta catcttccct gtacactggc agttcggcca gctggaccag     720
cacccattg acgggtacct ctcccacacc gagctggctc cactgcgtgc tcccctcatc     780
cccatggagc attgcaccac ccgctttttc gagacctgtg acctggacaa tgacaagtac     840
atcgccctgg atgagtgggc cggctgcttc ggcatcaagc agaaggatat cgacaaggat     900
cttgtgatct aa                                                         912
```

<210> SEQ ID NO 2
<211> LENGTH: 303
<212> TYPE: PRT
<213> ORGANISM: Homo sapiens

<400> SEQUENCE: 2

Met Arg Ala Trp Ile Phe Phe Leu Leu Cys Leu Ala Gly Arg Ala Leu
1               5                   10                  15

Ala Ala Pro Gln Gln Glu Ala Leu Pro Asp Glu Thr Glu Val Val Glu
            20                  25                  30

Glu Thr Val Ala Glu Val Thr Glu Val Ser Val Gly Ala Asn Pro Val
        35                  40                  45

Gln Val Glu Val Gly Glu Phe Asp Asp Gly Ala Glu Glu Thr Glu Glu
    50                  55                  60

Glu Val Val Ala Glu Asn Pro Cys Gln Asn His His Cys Lys His Gly
65                  70                  75                  80

Lys Val Cys Glu Leu Asp Glu Asn Asn Thr Pro Met Cys Val Cys Gln
                85                  90                  95

Asp Pro Thr Ser Cys Pro Ala Pro Ile Gly Glu Phe Glu Lys Val Cys
            100                 105                 110

Ser Asn Asp Asn Lys Thr Phe Asp Ser Ser Cys His Phe Phe Ala Thr
        115                 120                 125

Lys Cys Thr Leu Glu Gly Thr Lys Lys Gly His Lys Leu His Leu Asp
    130                 135                 140

Tyr Ile Gly Pro Cys Lys Tyr Ile Pro Pro Cys Leu Asp Ser Glu Leu
145                 150                 155                 160

```
Thr Glu Phe Pro Leu Arg Met Arg Asp Trp Leu Lys Asn Val Leu Val
                165                 170                 175
Thr Leu Tyr Glu Arg Asp Glu Asp Asn Leu Leu Thr Glu Lys Gln
        180                 185                 190
Lys Leu Arg Val Lys Lys Ile His Glu Asn Glu Lys Arg Leu Glu Ala
            195                 200                 205
Gly Asp His Pro Val Glu Leu Leu Ala Arg Asp Phe Glu Lys Asn Tyr
        210                 215                 220
Asn Met Tyr Ile Phe Pro Val His Trp Gln Phe Gly Gln Leu Asp Gln
225                 230                 235                 240
His Pro Ile Asp Gly Tyr Leu Ser His Thr Glu Leu Ala Pro Leu Arg
                245                 250                 255
Ala Pro Leu Ile Pro Met Glu His Cys Thr Thr Arg Phe Phe Glu Thr
                260                 265                 270
Cys Asp Leu Asp Asn Asp Lys Tyr Ile Ala Leu Asp Glu Trp Ala Gly
            275                 280                 285
Cys Phe Gly Ile Lys Gln Lys Asp Ile Asp Lys Asp Leu Val Ile
        290                 295                 300

<210> SEQ ID NO 3
<211> LENGTH: 78
<212> TYPE: DNA
<213> ORGANISM: Artificial Sequence
<220> FEATURE:
<223> OTHER INFORMATION: Synthetic human SPARC-siRNA 51

<400> SEQUENCE: 3
tggatcccgc ggcaggcaga gcgcgctctc ttgatatccg gagagcgcgc tctgcctgcc    60
gttttttcca actcgagg                                                 78

<210> SEQ ID NO 4
<211> LENGTH: 21
<212> TYPE: RNA
<213> ORGANISM: Artificial Sequence
<220> FEATURE:
<223> OTHER INFORMATION: Synthetic Rat siRNA

<400> SEQUENCE: 4
gagaagaacu acaacauguu u                                             21

<210> SEQ ID NO 5
<211> LENGTH: 21
<212> TYPE: RNA
<213> ORGANISM: Artificial Sequence
<220> FEATURE:
<223> OTHER INFORMATION: Synthetic Rat siRNA

<400> SEQUENCE: 5
ccagaaccau cauugcaaau u                                             21

<210> SEQ ID NO 6
<211> LENGTH: 21
<212> TYPE: RNA
<213> ORGANISM: Artificial Sequence
<220> FEATURE:
<223> OTHER INFORMATION: Synthetic Rat siRNA

<400> SEQUENCE: 6
gaacauugca ccacucgcuu u                                             21
```

```
<210> SEQ ID NO 7
<211> LENGTH: 21
<212> TYPE: RNA
<213> ORGANISM: Artificial Sequence
<220> FEATURE:
<223> OTHER INFORMATION: Synthetic Rat siRNA

<400> SEQUENCE: 7
cuacaucgga ccaugcaaau u                                              21

<210> SEQ ID NO 8
<211> LENGTH: 20
<212> TYPE: DNA
<213> ORGANISM: Artificial Sequence
<220> FEATURE:
<223> OTHER INFORMATION: Synthetic SPARC sense primer

<400> SEQUENCE: 8
ccacacgttt ctttgagacc                                                20

<210> SEQ ID NO 9
<211> LENGTH: 20
<212> TYPE: DNA
<213> ORGANISM: Artificial Sequence
<220> FEATURE:
<223> OTHER INFORMATION: Synthetic SPARC antisense primer

<400> SEQUENCE: 9
gatgtcctgc tccttgatgc                                                20

<210> SEQ ID NO 10
<211> LENGTH: 20
<212> TYPE: DNA
<213> ORGANISM: Artificial Sequence
<220> FEATURE:
<223> OTHER INFORMATION: Synthetic GAPDH sense primer

<400> SEQUENCE: 10
ggggctgccc agaacatcat                                                20

<210> SEQ ID NO 11
<211> LENGTH: 21
<212> TYPE: DNA
<213> ORGANISM: Artificial Sequence
<220> FEATURE:
<223> OTHER INFORMATION: Synthetic GAPDH antisense primer

<400> SEQUENCE: 11
gcctgcttca ccaccttctt g                                              21

<210> SEQ ID NO 12
<211> LENGTH: 20
<212> TYPE: DNA
<213> ORGANISM: Artificial Sequence
<220> FEATURE:
<223> OTHER INFORMATION: Synthetic TGF-B1 forward primer

<400> SEQUENCE: 12
accaactatt gcttcagctc                                                20

<210> SEQ ID NO 13
<211> LENGTH: 20
<212> TYPE: DNA
<213> ORGANISM: Artificial Sequence
<220> FEATURE:
<223> OTHER INFORMATION: Synthetic TGF-B1 reverse primer
```

```
<400> SEQUENCE: 13
tgttggttgt agagggcaag                                              20
```